US010980515B2

(12) United States Patent
Yamamoto

(10) Patent No.: US 10,980,515 B2
(45) Date of Patent: Apr. 20, 2021

(54) ACOUSTIC WAVE PROCESSING APPARATUS, SIGNAL PROCESSING METHOD, AND PROGRAM FOR ACOUSTIC WAVE PROCESSING APPARATUS

(71) Applicant: FUJIFILM Corporation, Tokyo (JP)

(72) Inventor: Hiroaki Yamamoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 736 days.

(21) Appl. No.: 15/255,841

(22) Filed: Sep. 2, 2016

(65) Prior Publication Data
US 2016/0367224 A1 Dec. 22, 2016

Related U.S. Application Data

(63) Continuation of application No. PCT/JP2015/050858, filed on Jan. 15, 2015.

(30) Foreign Application Priority Data

Mar. 26, 2014 (JP) .............................. JP2014-064084

(51) Int. Cl.
*A61B 8/08* (2006.01)
*A61B 8/14* (2006.01)
(Continued)

(52) U.S. Cl.
CPC .............. *A61B 8/5253* (2013.01); *A61B 8/14* (2013.01); *A61B 8/469* (2013.01); *A61B 8/5207* (2013.01);
(Continued)

(58) Field of Classification Search
CPC ......... A61B 8/5253; A61B 8/14; A61B 8/469; A61B 8/5207; A61B 8/4444;
(Continued)

(56) References Cited

U.S. PATENT DOCUMENTS 5,581,517 A * 12/1996 Gee ...................... G01S 7/52046
367/11
5,908,390 A * 6/1999 Matsushima ....... G01S 7/52023
600/447
(Continued)

FOREIGN PATENT DOCUMENTS

JP      58-44372 A    3/1983
JP   2006-141506 A    6/2006
(Continued)

OTHER PUBLICATIONS

English Translation of International Preliminary Report on Patentability (including PCT/IB/273 and PCT/ISA237) for PCT/JP2015/050858, dated Sep. 27, 2016.
(Continued)

*Primary Examiner* — Michael J Tsai
*Assistant Examiner* — Sean A Frith
(74) *Attorney, Agent, or Firm* — Birch, Stewart, Kolasch & Birch, LLP

(57) ABSTRACT

There are included a data processing step of selecting two or more pieces of data from among a plurality of pieces of first element data or a plurality of pieces of first reception data generated by subjecting the pieces of first element data to phasing addition processing, and performing superimposition processing on the two or more pieces of data, a region-of-interest setting step of setting a region of interest in an imaging area, and a processing condition changing step of changing a processing condition in the data processing step, in a case where the region of interest is set in the region-of-interest setting step, on the basis of information on the set region of interest.

20 Claims, 15 Drawing Sheets

(51) Int. Cl.
*A61B 8/00* (2006.01)
*G01S 7/52* (2006.01)
*G10K 11/34* (2006.01)
*G01S 15/89* (2006.01)

(52) U.S. Cl.
CPC ...... *G01S 7/52046* (2013.01); *G01S 7/52047* (2013.01); *G01S 7/52095* (2013.01); *G01S 15/8915* (2013.01); *G10K 11/346* (2013.01); *A61B 8/4444* (2013.01); *A61B 8/4488* (2013.01); *G01S 7/52063* (2013.01)

(58) Field of Classification Search
CPC ............... A61B 8/4488; G01S 7/52046; G01S 7/52047; G01S 7/52095; G01S 15/8915; G01S 7/52063; G10K 11/346
See application file for complete search history.

(56) References Cited

U.S. PATENT DOCUMENTS

| | | | | |
|---|---|---|---|---|
| 6,551,246 | B1* | 4/2003 | Ustuner | G01S 7/52026 600/447 |
| 2009/0182235 | A1 | 7/2009 | Robert et al. | |
| 2010/0234729 | A1* | 9/2010 | Bae | G01S 7/52028 600/441 |
| 2012/0044785 | A1* | 2/2012 | Yoda | G01S 7/52085 367/92 |
| 2012/0197127 | A1* | 8/2012 | Nakamura | G01S 7/52025 600/447 |
| 2013/0258805 | A1* | 10/2013 | Hansen | A61B 8/14 367/8 |
| 2014/0309531 | A1* | 10/2014 | Eda | A61B 8/469 600/443 |
| 2014/0313856 | A1* | 10/2014 | Taki | A61B 8/14 367/87 |
| 2015/0141831 | A1 | 5/2015 | Yamamoto | |

FOREIGN PATENT DOCUMENTS

| | | | | |
|---|---|---|---|---|
| JP | 2009-536853 A | 10/2009 | | |
| JP | 2014-30715 A | 2/2014 | | |
| WO | WO-2012032848 A1 * | 3/2012 | ............ | A61B 8/4472 |

OTHER PUBLICATIONS

Japanese Notification of Reasons of Refusal, dated Jun. 6, 2017, for corresponding Japanese Application No. 2014-064084, with an English machine translation.
International Search Report for PCT/JP2015/050858 (PCT/ISA/210) dated Apr. 7, 2015.
Written Opinion of the International Searching Authority for PCT/JP2015/050858 (PCT/ISA/237) dated Apr. 7, 2015.
Japanese Office Action for Japanese Application No. 2014-064084, dated Nov. 1, 2016, with a machine translation.

* cited by examiner

ELEMENT DATA

ELEMENT DATA

ELEMENT DATA

ELEMENT DATA

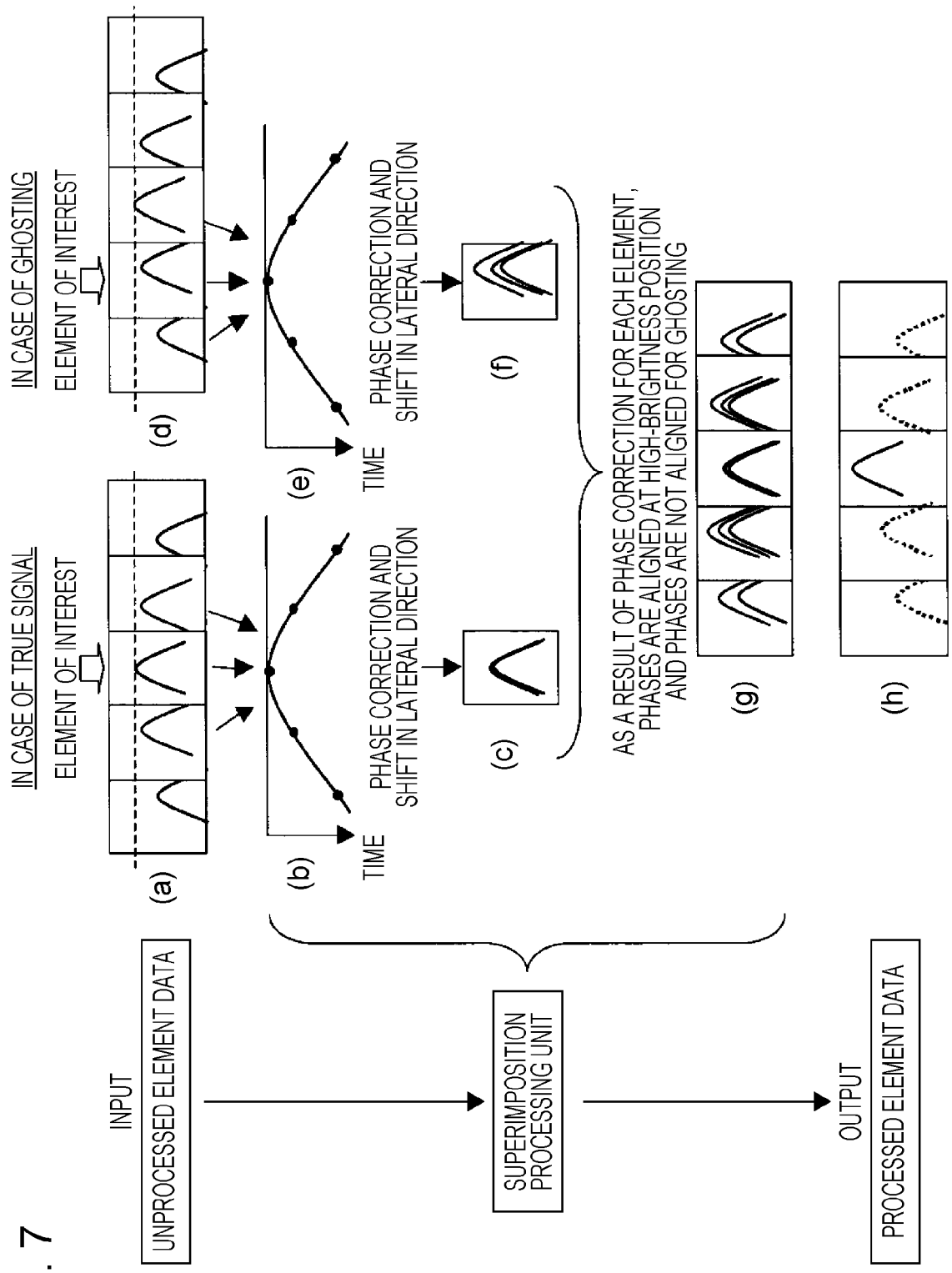

ACOUSTIC WAVE PROCESSING APPARATUS, SIGNAL PROCESSING METHOD, AND PROGRAM FOR ACOUSTIC WAVE PROCESSING APPARATUS

CROSS-REFERENCE TO RELATED APPLICATIONS

This application is a Continuation of PCT International Application No. PCT/JP2015/050858 filed on Jan. 15, 2015, which claims priority under 35 U.S.C § 119 (a) to Japanese Patent Application No. 2014-064084 filed on Mar. 26, 2014. Each of the above application(s) is hereby expressly incorporated by reference, in its entirety, into the present application.

BACKGROUND OF THE INVENTION

1. Field of the Invention

The present invention relates to an acoustic wave processing apparatus, a signal processing method, and a non-transitory computer readable recording medium storing a program for imaging an inspection object, such as an organ in a living body, by transmitting and receiving acoustic wave beams to generate acoustic wave images or the like used for the examination or diagnosis of the inspection object.

2. Description of the Related Art

In the field of medicine, acoustic-wave diagnostic apparatuses, such as ultrasonic image diagnostic apparatuses, that generate ultrasound images used for the examination or diagnosis of an inspection object by using acoustic waves, such as ultrasonic waves, are conventionally put to practical use.

This type of ultrasonic diagnostic apparatus typically has an ultrasonic probe (ultrasonic probe unit: hereinafter also referred to as "probe") having a plurality of elements (ultrasonic transducers) built therein, and an apparatus body connected to the probe. The ultrasonic diagnostic apparatus transmits ultrasonic beams from the plurality of elements of the probe toward a subject (an inspection object) so as to form a predetermined focal point (transmit focal point), receives ultrasonic echoes from the subject by using the probe, and electrically processes reception signals of the received ultrasonic echoes by using the apparatus body to thereby generate an ultrasound image.

An ultrasonic beam is transmitted on the basis of a predetermined transmit delay pattern so as to drive a plurality of elements to form a set focal point. Such an ultrasonic beam is shaped to be wide in the lateral direction. This causes a problem in that information on a reflection point located at a laterally shifted position may be picked up and reproduced on an ultrasound image as a so-called "ghost" signal.

To address this problem, in the ultrasonic diagnostic apparatus, the generation of a single ultrasound image includes superimposing a plurality of pieces of data (element data or reception data) obtained via individual transmissions in accordance with reception times or the positions of the elements and correcting the pieces of data, called multi-line processing (JPS58-44372A (JP1983-44372A) and JP2009-536853A). Ghost signals are removable because the ghost signals are superimposed while being shifted with respect to each other and cancel each other out even if pieces of data are superimposed in accordance with reception times or the positions of the elements.

SUMMARY OF THE INVENTION

In an ultrasonic diagnostic apparatus that performs multi-line processing, however, if a region of interest is set in an imaging area, in some cases, processing conditions for the multi-line processing may include a processing condition that is not appropriate for the set region of interest. Thus, there is a concern that a reduction in image quality or a reduction in frame rate may occur in the region of interest.

It is an object of the present invention to overcome the problems with the conventional technique described above and to provide an acoustic wave processing apparatus, a signal processing method, and a non-transitory computer readable recording medium storing a program that can provide, when a region of interest is set in an ultrasonic diagnostic apparatus which performs multi-line processing, an image of the region of interest with high quality and can prevent a reduction in frame rate within the region of interest.

As a result of intensive studies to achieve the foregoing object, the inventor has found that the problems described above can be overcome by the provision of a data processing unit that selects two or more pieces of data from among a plurality of pieces of first element data or a plurality of pieces of first reception data generated by subjecting the pieces of first element data to phasing addition processing and that performs superimposition processing on the two or more pieces of data, a region-of-interest setting unit that sets a region of interest in an imaging area, and a processing condition changing unit that changes, in a case where the region of interest is set by the region-of-interest setting unit, a processing condition in the data processing unit on the basis of information on the set region of interest.

Specifically, the present invention provides (1) to (13) as follows.

(1) An acoustic wave processing apparatus including:

a probe unit having a plurality of elements arranged therein, the probe unit being configured to transmit an acoustic wave beam, receive an acoustic wave echo reflected by an inspection object that has received the transmitted acoustic wave beam, and output an analog element signal corresponding to the received acoustic wave echo;

a transmitting unit that causes the probe unit to transmit the acoustic wave beam a plurality of times by using two or more elements among the plurality of elements as transmit elements to form a predetermined transmit focal point;

a receiving unit that receives an acoustic echo corresponding to each transmission of the acoustic beam with two or more elements among the plurality of elements as reception elements, receives analog element signals output from the reception elements, and performs predetermined processing on the analog element signals;

an A/D conversion unit that performs A/D conversion on the analog element signals processed by the receiving unit to convert the analog element signals to first element data as a digital element signal;

a data processing unit that selects two or more pieces of data from among a plurality of pieces of the first element data output by the A/D conversion unit or from among a plurality of pieces of first reception data generated by performing phasing addition processing on the first element data and performs superimposition processing on the selected two or more pieces of data;

a region-of-interest setting unit that sets a region of interest in an imaging area; and a processing condition changing unit that changes, in a case where the region of interest is set by the region-of-interest setting unit, a processing condition in the data processing unit on the basis of information on the set region of interest.

(2) The acoustic wave processing apparatus according to (1), wherein the data processing unit selects two or more pieces of first element data from among the plurality of pieces of first element data, and superimposes the selected two or more pieces of first element data in accordance with reception times at which the elements receive the acoustic wave echo and positions of the elements to generate second element data.

(3) The acoustic wave processing apparatus according to (1), further including a phasing addition unit that performs phasing addition on each of the pieces of first element data by using at least two elements as references to generate at least two pieces of first reception data for each of the pieces of first element data, wherein the data processing unit selects two or more pieces of first reception data from among the plurality of pieces of first reception data, and superimposes the selected two or more pieces of first reception data in accordance with reception times at which the elements receive the acoustic wave echo and positions of the elements to generate second reception data.

(4) The acoustic wave processing apparatus according to (3), wherein the data processing unit superimposes two or more pieces of first reception data that are generated from the pieces of first element data, which are different from each other, and that are generated by subjecting the different pieces of first element data to phasing addition processing by using an identical element as a reference.

(5) The acoustic wave processing apparatus according to any of (1) to (4), wherein the processing condition changing unit changes at least one of the number of pieces of data to be superimposed, an apodization factor, a sound velocity, and a delay time in the data processing unit.

(6) The acoustic wave processing apparatus according to any of (1) to (5), wherein the processing condition changing unit changes a processing condition in the data processing unit on the basis of information on at least one of a size, position, and shape of the set region of interest.

(7) The acoustic wave processing apparatus according to any of (1) to (6), further including a processing condition change determination unit that determines whether or not to change the processing condition by using the processing condition changing unit in a case where the region of interest is set by the region-of-interest setting unit.

(8) The acoustic wave processing apparatus according to (7), wherein the processing condition change determination unit determines whether or not to change the processing condition on the basis of information on the set region of interest.

(9) The acoustic wave processing apparatus according to (7), wherein the processing condition change determination unit determines whether or not to change the processing condition in accordance with an instruction input from an operation unit.

(10) The acoustic wave processing apparatus according to any of (1) to (9), further including a setting information saving unit that saves a processing condition changed by the processing condition changing unit.

(11) The acoustic wave processing apparatus according to any of (1) to (10), wherein the transmitting unit causes the probe unit to transmit the acoustic wave beam the plurality of times by at least either changing an element serving as a center or changing a transmit direction of the acoustic wave beam.

(12) A signal processing method for an acoustic wave processing apparatus for examining an inspection object by using a probe unit having a plurality of elements arranged therein, the probe unit being configured to transmit an acoustic wave beam, receive an acoustic wave echo reflected by the inspection object, which has received the transmitted acoustic wave beam, and output an analog element signal corresponding to the received acoustic wave echo, the signal processing method including:

a transmitting step of transmitting the acoustic wave beam a plurality of times by using two or more elements among the plurality of elements of the probe unit as transmit elements to form a predetermined transmit focal point;

a receiving step of receiving an acoustic echo corresponding to each transmission of the acoustic beam with two or more elements among the plurality of elements as reception elements, receiving analog element signals output from the reception elements, and performing predetermined processing on the analog element signals;

an A/D conversion step of performing A/D conversion on the analog element signals processed in the receiving step to convert the analog element signals to first element data as a digital element signal;

a data processing step of selecting two or more pieces of data from among a plurality of pieces of the first element data output in the A/D conversion step or from among a plurality of pieces of first reception data generated by performing phasing addition processing on the first element data, and performing superimposition processing on the selected two or more pieces of data;

a region-of-interest setting step of setting a region of interest in an imaging area; and a processing condition changing step of changing a processing condition in the data processing step, in a case where the region of interest is set in the region-of-interest setting step, on the basis of information on the set region of interest.

(13) A non-transitory computer readable recording medium storing a signal processing program for an acoustic wave processing apparatus, the signal processing program being a program for causing a computer to execute a signal processing method for the acoustic wave processing apparatus for examining an inspection object by using a probe unit having a plurality of elements arranged therein, the probe unit being configured to transmit an acoustic wave beam, receive an acoustic wave echo reflected by the inspection object, which has received the transmitted acoustic wave beam, and output an analog element signal corresponding to the received acoustic wave echo, the signal processing program causing the computer to execute:

a transmitting step of transmitting the acoustic wave beam a plurality of times by using two or more elements among the plurality of elements of the probe unit as transmit elements to form a predetermined transmit focal point;

a receiving step of receiving an acoustic echo corresponding to each transmission of the acoustic beam with two or more elements among the plurality of elements as reception elements, receiving analog element signals output from the reception elements, and performing predetermined processing on the analog element signals;

an A/D conversion step of performing A/D conversion on the analog element signals processed in the receiving step to convert the analog element signals to first element data as a digital element signal;

a data processing step of selecting two or more pieces of data from among a plurality of pieces of the first element data output in the A/D conversion step or from among a plurality of pieces of first reception data generated by performing phasing addition processing on the first element data, and performing superimposition processing on the selected two or more pieces of data;

a region-of-interest setting step of setting a region of interest in an imaging area; and a processing condition changing step of changing a processing condition in the data processing step, in a case where the region of interest is set in the region-of-interest setting step, on the basis of information on the set region of interest.

According to an aspect of the present invention, it is possible to provide an acoustic wave processing apparatus, a signal processing method, and a non-transitory computer readable recording medium storing a program that can obtain, when a region of interest is set in an acoustic wave processing apparatus which performs multi-line processing, a high-quality image of the region of interest and can prevent a reduction in frame rate within the region of interest.

Figure 1:
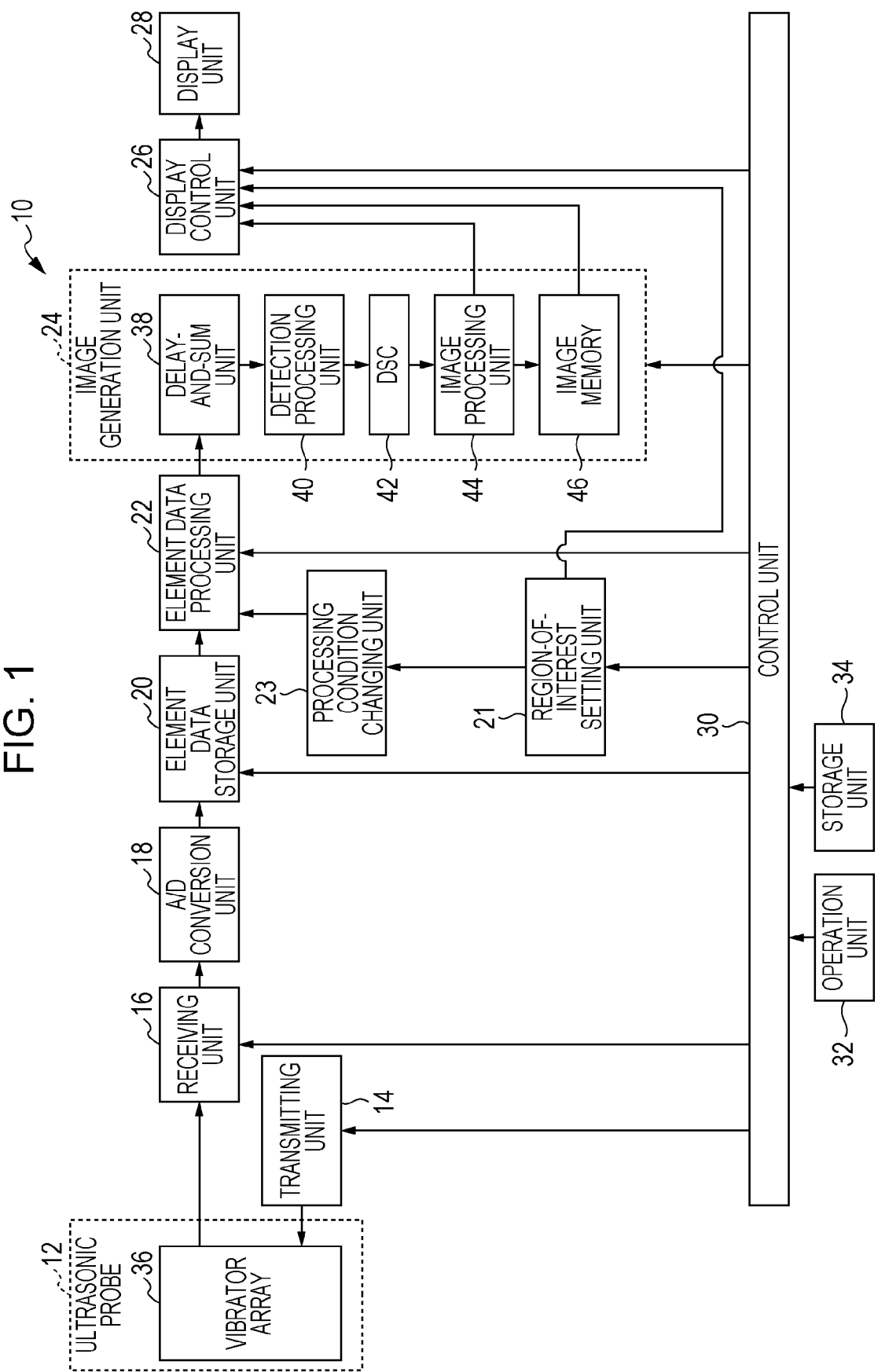
FIG. 1 is a block diagram conceptually illustrating an example of the configuration of an ultrasonic diagnostic apparatus of the present invention.
Figure 8A:
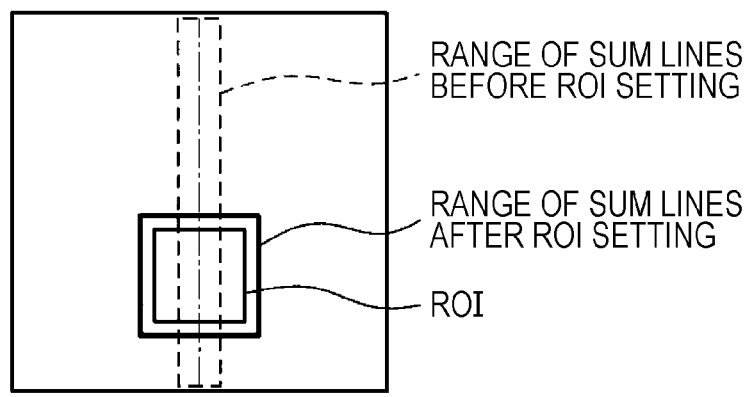
Figure 8B:
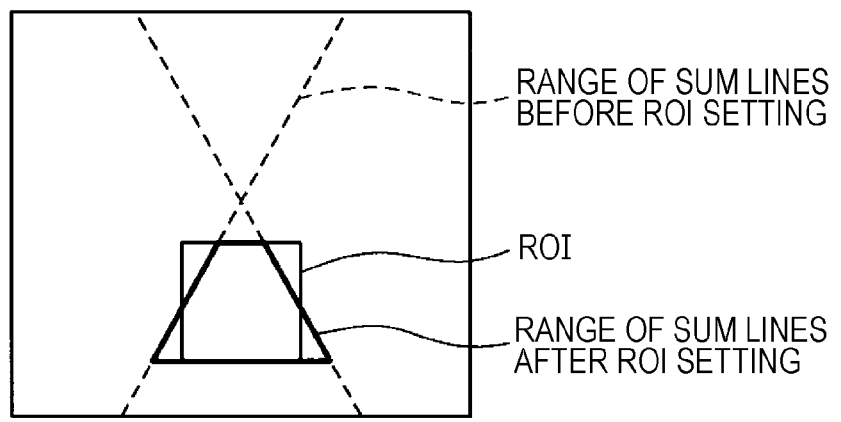
Figure 9:
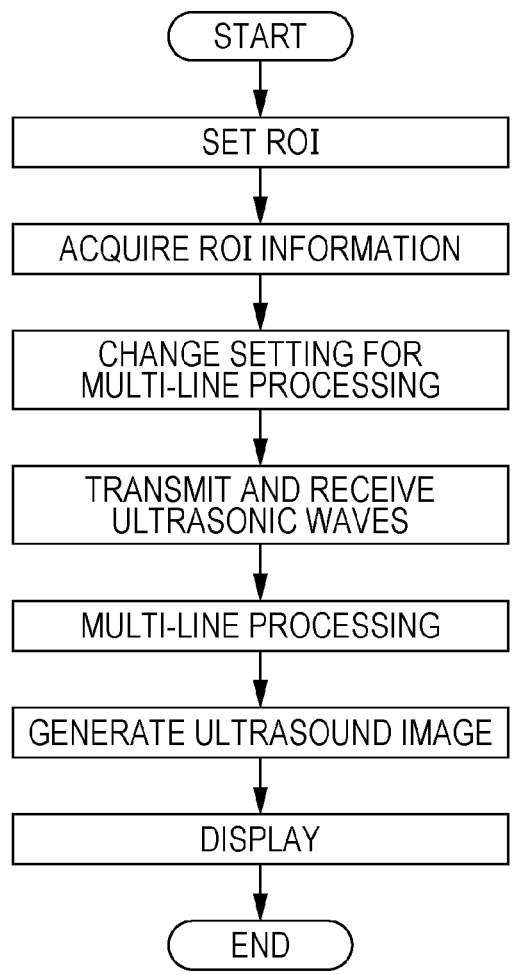
Figure 10:
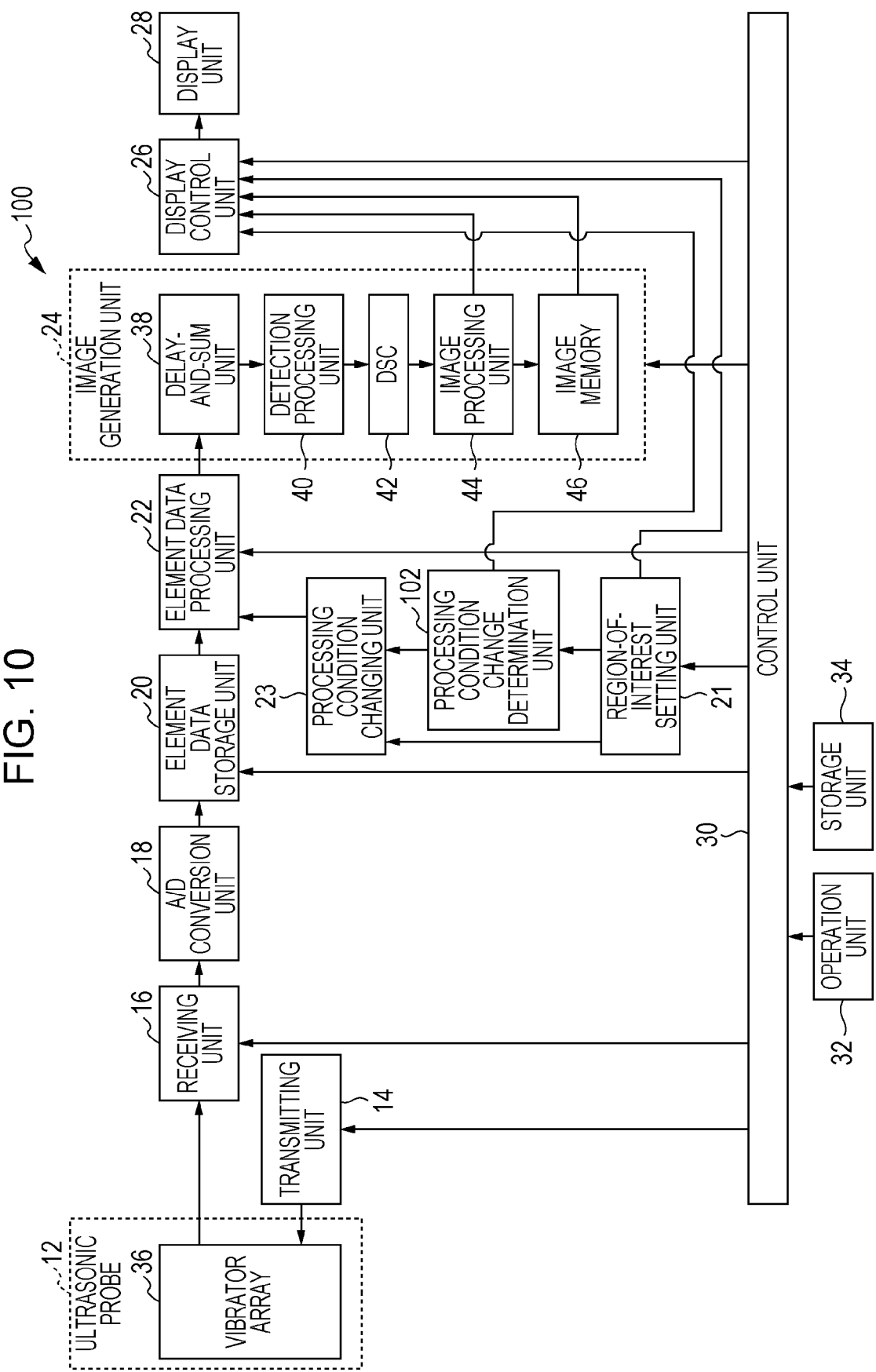
Figure 11:
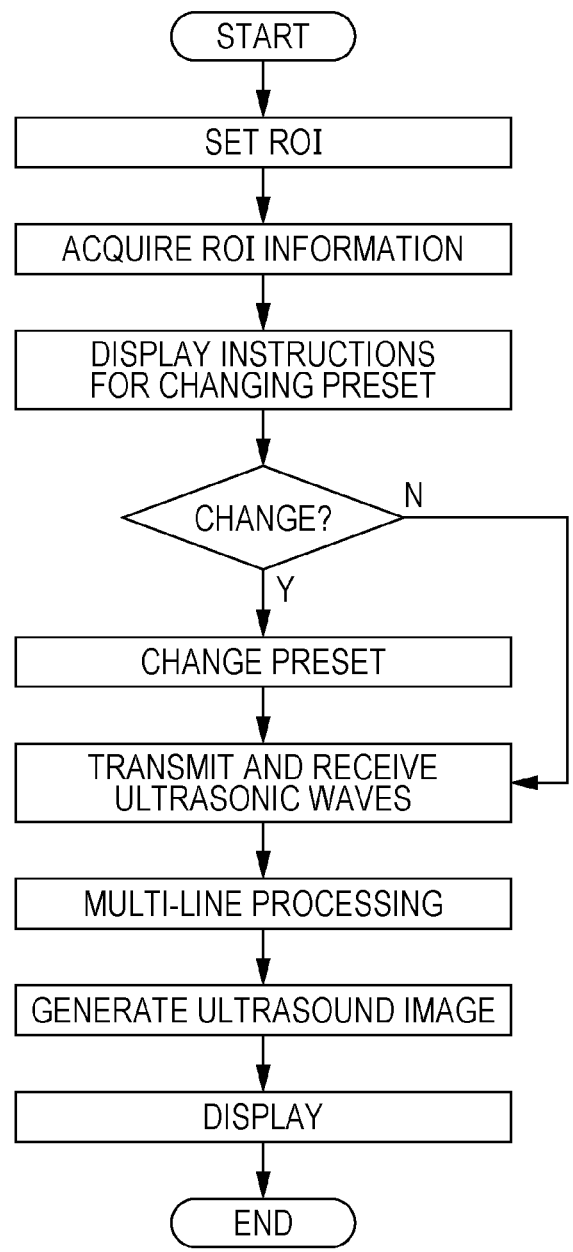
Figure 12:
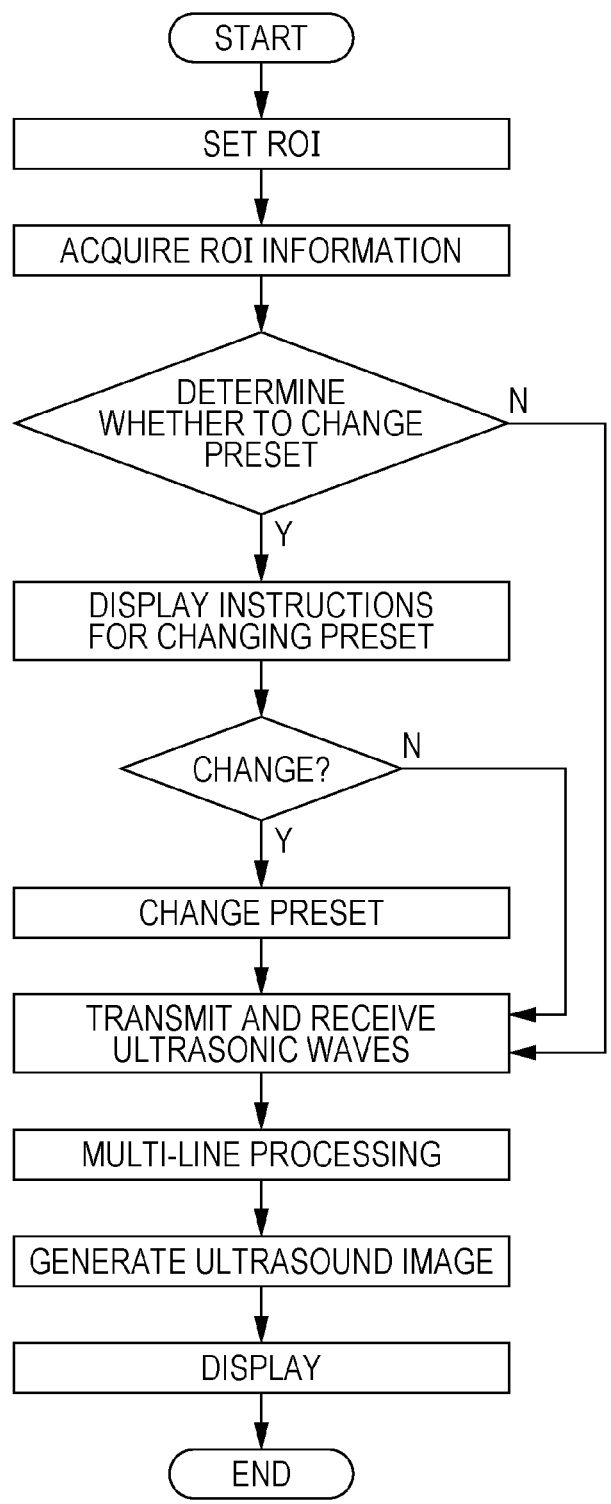
Figure 13:
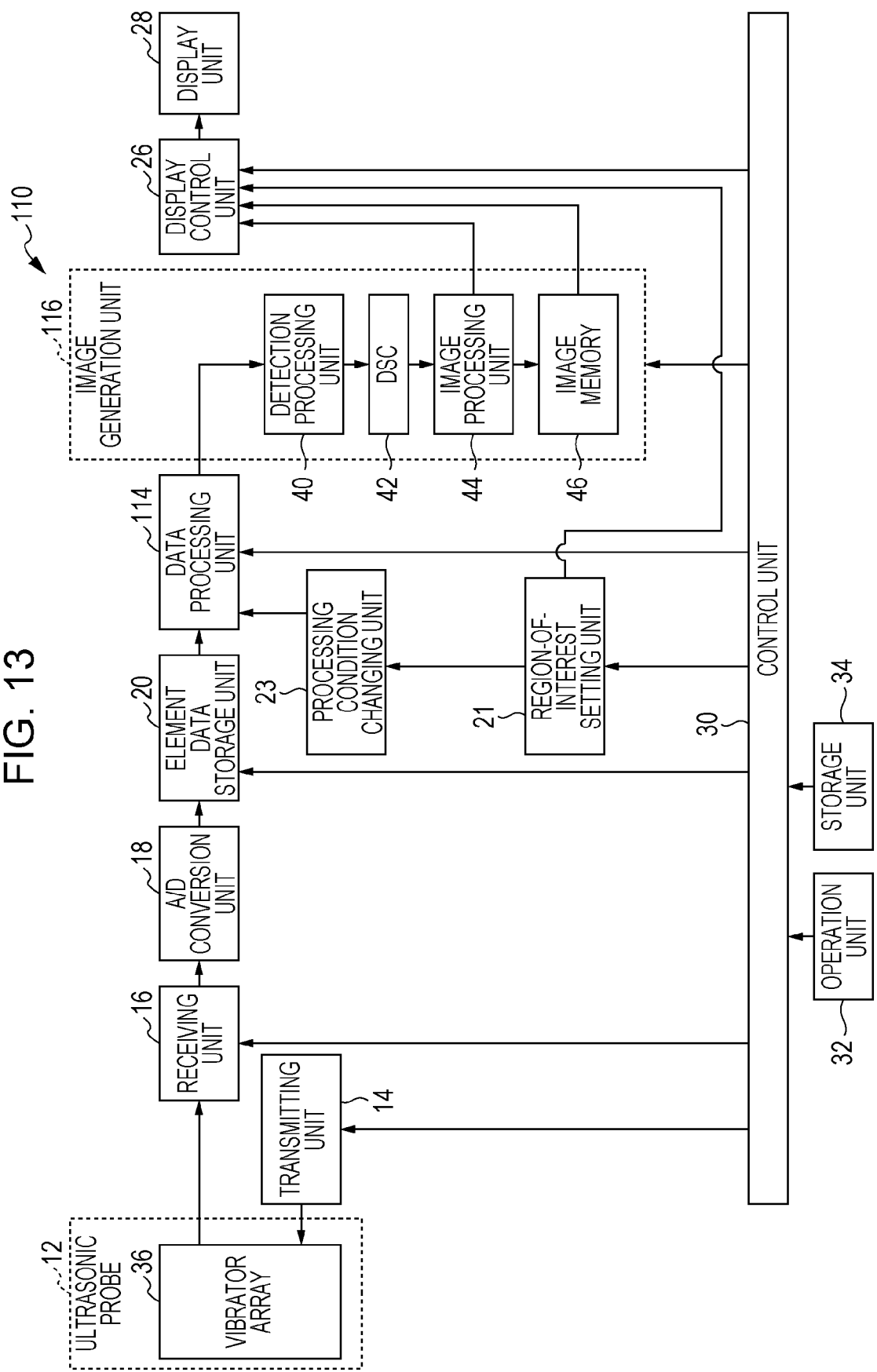
Figure 14:
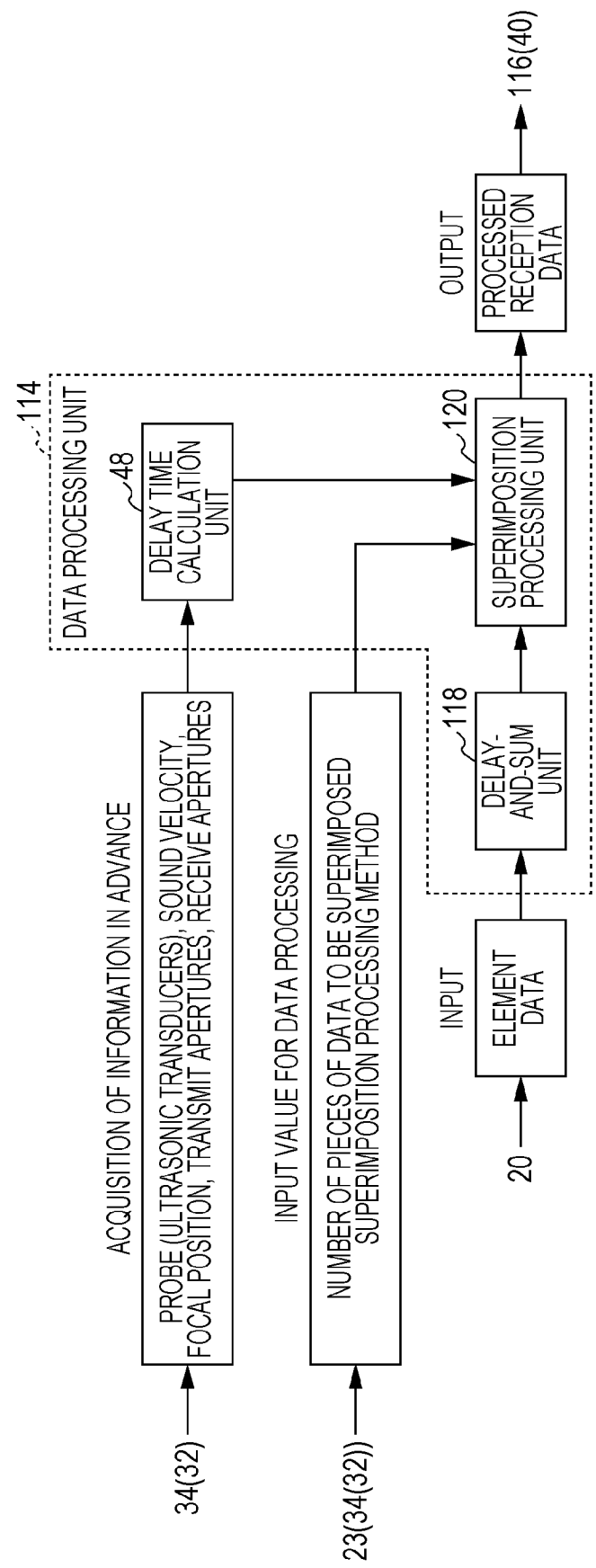
Figure 15:
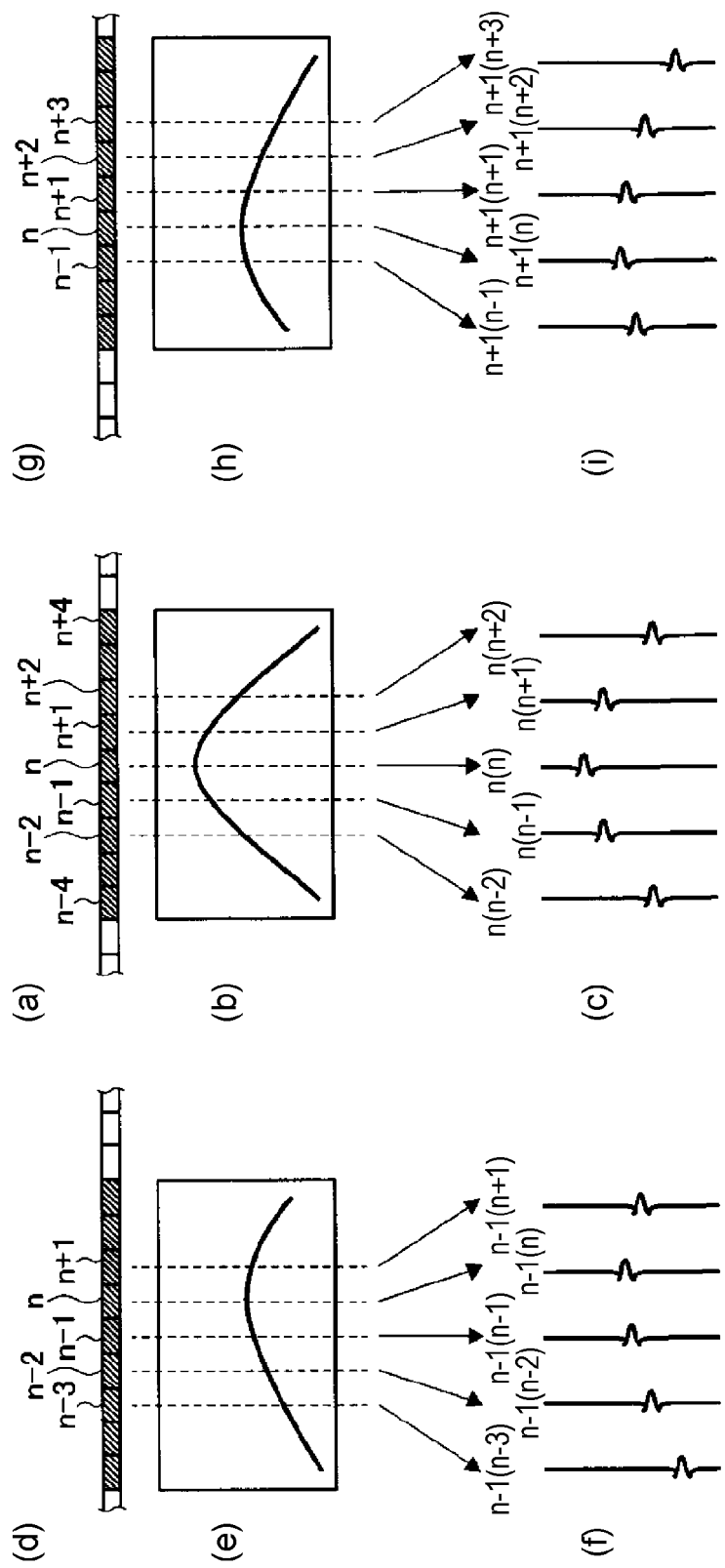
Figure 16:
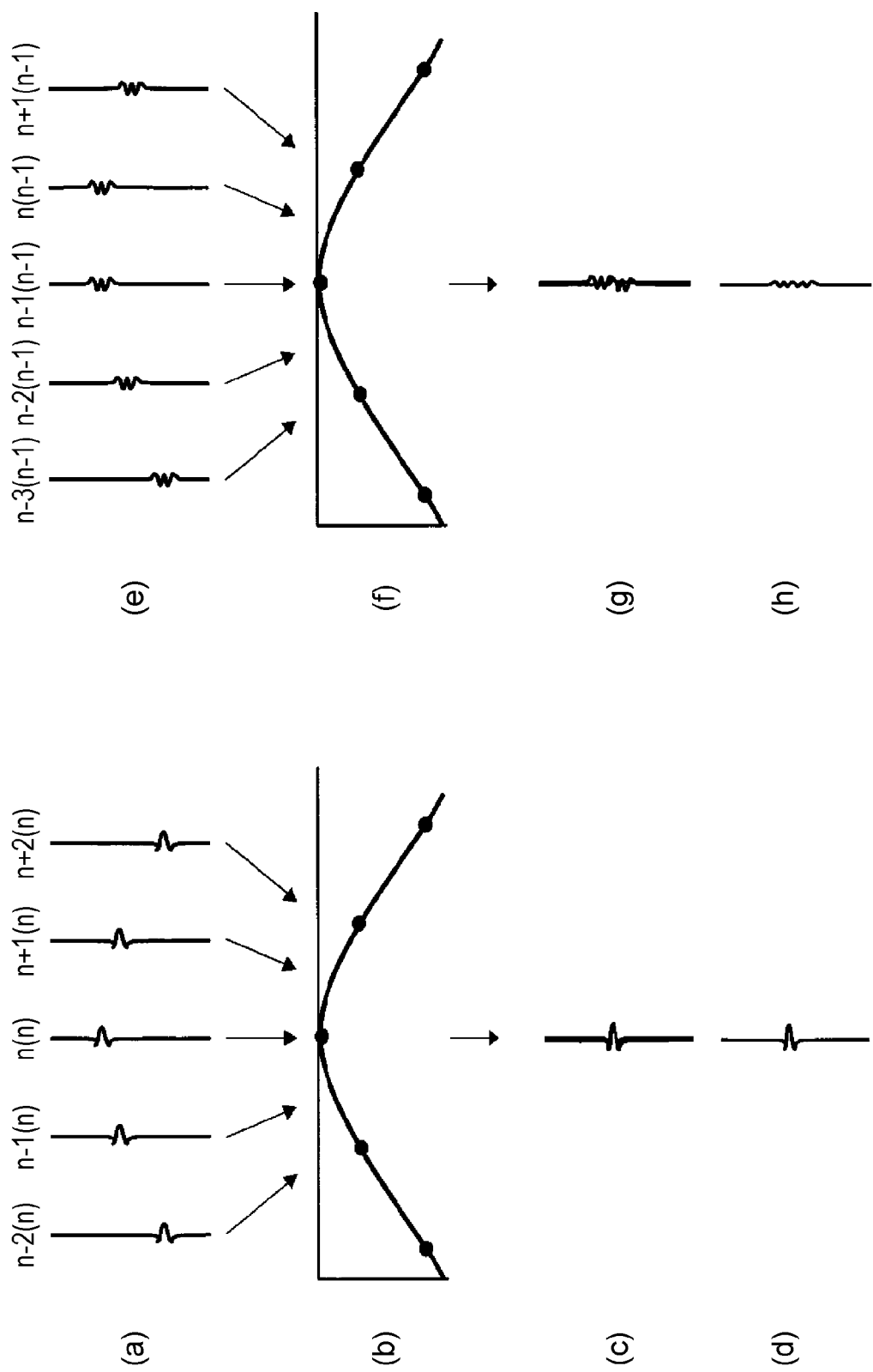

Parts (a), (b), and (c) of FIG. 7 are conceptual diagrams for respectively describing element data of a true signal, their delay times, and the state of superimposed element data, parts (d), (e), and (f) of FIG. 7 are conceptual diagrams for respectively describing element data for ghosting, their delay times, and the state of superimposed element data, part (g) of FIG. 7 is a conceptual diagram for describing states of superimposed element data corresponding to a plurality of elements, and part (h) of FIG. 7 is a conceptual diagram for describing the result of superimposition of the element data in part (g) of FIG. 7;

FIG. 8A and FIG. 8B are conceptual diagrams for describing a range of sum lines after ROI setting;

FIG. 9 is a flowchart for describing an operation of the ultrasonic diagnostic apparatus illustrated in FIG. 1;

FIG. 10 is a block diagram conceptually illustrating another example of the configuration of the ultrasonic diagnostic apparatus of the present invention;

FIG. 11 is a flowchart for describing an operation of the ultrasonic diagnostic apparatus illustrated in FIG. 10;

FIG. 12 is a flowchart for describing an operation of another example of the ultrasonic diagnostic apparatus illustrated in FIG. 10;

FIG. 13 is a block diagram conceptually illustrating another example of the configuration of the ultrasonic diagnostic apparatus of the present invention;

FIG. 14 is a block diagram conceptually illustrating an example of the configuration of a data processing unit of the ultrasonic diagnostic apparatus illustrated in FIG. 13;

Parts (a), (d), and (g) of FIG. 15 are conceptual diagrams for describing individual receive elements, parts (b), (e), and (h) of FIG. 15 are conceptual diagrams illustrating element data obtained by each transmission and reception of ultrasonic waves, and parts (c), (f), and (i) of FIG. 15 are conceptual diagrams illustrating unprocessed reception data obtained by subjecting individual pieces of element data to phasing addition processing; and Parts (a) and (e) of FIG. 16 are each a conceptual diagram illustrating unprocessed reception data to be subjected to superimposition, parts (b) and (f) of FIG. 16 are conceptual diagrams for describing their delay times, parts (c) and (g) of FIG. 16 are conceptual diagrams for describing the state of superimposed unprocessed reception data, and parts (d) and (h) of FIG. 16 are conceptual diagrams for describing the result of superimposition of the unprocessed reception data.

DESCRIPTION OF THE PREFERRED EMBODIMENTS

An acoustic wave processing apparatus, a program of the present invention will be described in detail hereinafter based on a preferred first embodiment illustrated in the accompanying drawings.

While an ultrasonic wave is employed as an acoustic wave in embodiments of the present invention, the acoustic wave is not limited to an ultrasonic wave and an acoustic wave having an audible frequency may be used as long as an appropriate frequency is selected in accordance with the examination target, the measurement conditions, and so on.

FIG. 1 conceptually illustrates in block diagram form an example of an ultrasonic diagnostic apparatus (acoustic wave processing apparatus) of the present invention.

As illustrated in FIG. 1, an ultrasonic diagnostic apparatus 10 includes an ultrasonic probe 12, a transmitting unit 14 and a receiving unit 16, which are connected to the ultrasonic probe 12, an A/D conversion unit 18, an element data storage unit 20, a region-of-interest setting unit 21, an element data processing unit 22, a processing condition changing unit 23, an image generation unit 24, a display control unit 26, a display unit 28, a control unit 30, an operation unit 32, and a storage unit 34.

In the illustrated example, the transmitting unit 14, the receiving unit 16, the A/D conversion unit 18, the element data storage unit 20, the region-of-interest setting unit 21, the element data processing unit 22, the processing condition changing unit 23, the image generation unit 24, the display control unit 26, the display unit 28, the control unit 30, the operation unit 32, and the storage unit 34 constitute an apparatus body of the ultrasonic diagnostic apparatus 10.

The ultrasonic probe (ultrasonic probe unit) 12 is a well-known ultrasonic probe used in a typical ultrasonic diagnostic apparatus.

The ultrasonic probe 12 (hereinafter referred to as the probe 12) includes a vibrator array 36 configured such that ultrasonic transducers are arranged one-dimensionally or two-dimensionally.

When imaging an ultrasound image of an inspection object (hereinafter referred to as a subject), the ultrasonic transducers transmit ultrasonic beams to the subject in accordance with respective drive signals supplied from the transmitting unit 14, and, in addition, receive ultrasonic echoes reflected by the subject and output reception signals corresponding to the intensities of the received ultrasonic waves.

Each of the ultrasonic transducers is constituted by a vibrator having an electrode at either end of a piezoelectric body composed of, for example, a piezoelectric ceramic such as PZT (lead zirconate titanate), a polymer piezoelectric element such as that made of PVDF (polyvinylidene fluoride), or a piezoelectric single crystal such as PMN-PT (lead magnesium niobate-lead titanate solid solution).

When a pulsed or continuous-wave voltage is applied to the electrodes of the vibrator, the piezoelectric body expands and contracts in accordance with the applied voltage, causing a pulsed or continuous-wave ultrasonic wave to emanate from each vibrator. The ultrasonic waves emanating from the respective vibrators converge to a set focal point and are combined (that is, transmit-focused) in accordance with the respective driving delays of the vibrators to thereby form an ultrasonic beam.

In addition, the vibrators expand and contract in response to incoming ultrasonic echoes which are reflected within the subject, and produce electrical signals in accordance with the magnitude of the expansion and contraction. The electrical signals are output to the receiving unit 16 as reception signals (analog element signals).

The transmitting unit 14 includes a plurality of pulsers, for example, and supplies drive signals (applies drive voltages) to the respective ultrasonic transducers (vibrators) of the probe 12.

The transmitting unit 14 performs transmit-focusing for adjusting amounts of delay of the drive signals (the application timings of the drive voltages) on the basis of transmit delay patterns selected by the control unit 30 so as to form an ultrasonic beam in such a manner that ultrasonic waves transmitted from a predetermined number of (a plurality of) ultrasonic transducers converge to a set focal point, and supplies the drive signals to the ultrasonic transducers.

Thus, an intended ultrasonic beam is transmitted to the subject from the probe 12 (the vibrator array 36).

In accordance with a control signal from the control unit 30, the receiving unit 16 receives reception signals output from the predetermined number of (the plurality of) ultrasonic transducers in response to a single transmission of an ultrasonic beam, performs predetermined processing such as amplification, and supplies the resulting signals to the A/D conversion unit 18.

Note that, in the ultrasonic diagnostic apparatus 10 of the present invention, the method for transmission and reception of an ultrasonic wave is basically similar to that in a well-known ultrasonic diagnostic apparatus.

Thus, in a single transmission and reception of ultrasonic waves (transmission of a single ultrasonic beam and reception of an ultrasonic echo in response to this transmission), there is no limitation on the number of ultrasonic transducers (the number of transmit apertures) that produce ultrasonic waves or the number of ultrasonic transducers (the number of receive apertures) that receive ultrasonic waves (from which the receiving unit 16 receives reception signals) as long as the numbers are both plural. In a single transmission and reception, furthermore, the numbers of apertures for transmission and reception may be the same or different.

In addition, there is also no limitation on the number of transmissions and receptions of ultrasonic waves (the number of sound rays) for forming a single ultrasound image or the spacing of an ultrasonic transducer (central element) on which transmission and reception are centered (that is, the density of scan lines/sound rays) as long as ultrasonic beams adjacent in at least the azimuth direction (the arrangement direction of the ultrasonic transducers) have overlapping transmit areas. Thus, transmission and reception of ultrasonic waves may be performed by using as central elements all the ultrasonic transducers corresponding to an area scanned with ultrasonic waves, or transmission and reception of ultrasonic waves may be performed by using as central elements ultrasonic transducers spaced apart at predetermined intervals such as every two or four transducers.

Furthermore, in a manner similar to that in a well-known ultrasonic diagnostic apparatus, transmission and reception are performed at a plurality of positions (lines) with the sequential movement of transmit and receive positions to form a single ultrasound image.

The A/D conversion unit 18 performs analog/digital conversion on the analog reception signals (analog element signals) supplied from the receiving unit 16 into element data (first element data) that is digital reception signals (digital element signals).

The A/D conversion unit 18 supplies the element data subjected to A/D conversion to the element data storage unit 20.

The element data storage unit 20 sequentially stores the element data supplied from the A/D conversion unit 18. The element data storage unit 20 further stores information related to the frame rate (for example, parameters indicating the depth of the reflection position of the ultrasonic wave, the density of the scan lines, and the width of the field of view), which is input from the control unit 30, in association with each piece of element data.

Preferably, the element data storage unit 20 stores all pieces of element data corresponding to at least one ultrasound image (an ultrasound image of one frame) and does not delete the element data of the ultrasound image currently being displayed or an ultrasound image yet to be displayed at least until the display of the ultrasound image is completed.

The region-of-interest setting unit 21 is a part that sets a region of interest ROI within the subject.

There is no particular limitation on the method for setting a region of interest ROI by using the region-of-interest setting unit 21, and various well-known methods for setting a region of interest ROI can be used. For example, while viewing an ultrasound image displayed on the display unit 28, an operator operates the operation unit 32 to display a frame representing an ROI in such a manner that the frame is overlaid on the ultrasound image, and moves, scales, and deforms the frame representing the ROI, which is displayed overlaid on the ultrasound image, to give instructions as to the position, size, and shape of the region of interest ROI. The region-of-interest setting unit 21 sets the region of interest ROI in accordance with an input operation given from the operation unit 32. In this case, for example, the case in which instructions indicating the determination of the region of interest ROI have been input may be regarded as the setting of the region of interest ROI, or the case in which the frame representing the ROI is stationary for a predetermined amount of time (during a predetermined number of frames) may be regarded as the setting of the region of interest ROI. Alternatively, the point in time at which the operation of setting the region of interest ROI is started may be regarded as the setting of the region of interest ROI.

The region-of-interest setting unit 21 supplies information on the set region of interest ROI to the processing condition changing unit 23 and the display control unit 26.

The element data processing unit 22 is a part that superimposes element data to generate processed element data (second element data) corresponding to each piece of element data.

Specifically, the element data processing unit 22 superimposes, among the pieces of element data stored in the element data storage unit 20, pieces of element data obtained by transmitting a predetermined number of (a plurality of) ultrasonic beams for which the ultrasonic transducers serving as the centers (the elements serving as the centers (central elements)) are different and which have overlapping transmit areas, on the basis of the control by the control unit 30 and processing condition information from the processing condition changing unit 23, in accordance with the times at which the respective ultrasonic transducers receive the ultrasonic echoes (the delay times) and the positions of the ultrasonic transducers, thereby generating processed element data corresponding to element data (element data of an element of interest described below).

The process performed in the element data processing unit 22 will be described in detail below.

The element data processing unit 22 delivers the generated processed element data to the image generation unit 24.

The processing condition changing unit 23 is a part that changes a condition for the processing of element data in the element data processing unit 22 on the basis of the information on the region of interest set by the region-of-interest setting unit 21.

Specifically, the processing condition changing unit 23 changes (sets) at least one condition among the number of superimpositions for superimposition processing performed in the element data processing unit 22, a weighting factor for superimposition (an apodization factor), a delay time used for superimposition, and a sound-velocity value used for calculation of a delay time, on the basis of information on at least one of the size, position, and shape of the region of interest.

This point will be described in detail below.

The processing condition changing unit 23 supplies information on the set processing condition to the element data processing unit 22.

The image generation unit 24 is configured to generate reception data (sound ray signals) from the processed element data supplied from the element data processing unit 22 on the basis of the control by the control unit 30 and to generate an ultrasound image from the reception data.

The image generation unit 24 includes a phasing addition unit 38, a detection processing unit 40, a DSC 42, an image processing unit 44, and an image memory 46.

The phasing addition unit 38 executes phasing addition on the processed element data generated by the element data processing unit 22 to perform a receive-focusing process, and generates reception data.

As described above, the vibrator array 36 of the probe 12 is configured such that a plurality of elements (ultrasonic transducers) are arranged one-dimensionally or two-dimensionally. Thus, the distance to a single reflection point in the subject differs from one ultrasonic transducer to another. This causes even ultrasonic echoes reflected at the same reflection point to arrive at the individual ultrasonic transducers at different times. The phasing addition unit 38 delays each signal of the processed element data by an amount corresponding to an arrival time difference (delay time) of the ultrasonic echo for each ultrasonic transducer in accordance with a receive delay pattern selected by the control unit 30, and executes phasing addition on the processed element data to which the respective delay times are applied to perform a receive-focusing process digitally, thereby generating reception data.

The phasing addition unit 38 supplies the generated reception data to the detection processing unit 40.

Figure 2:
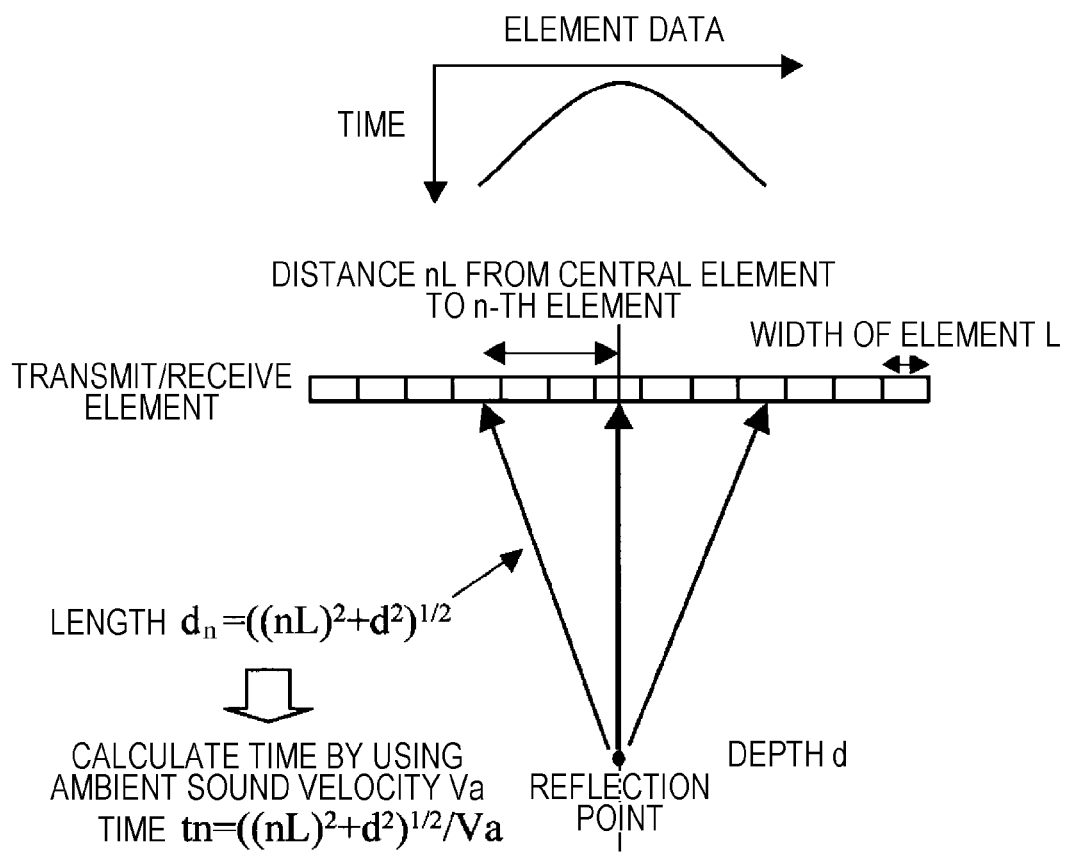
FIG. 2 is a conceptual diagram for describing an example of a receive-focusing process in the ultrasonic diagnostic apparatus illustrated in FIG. 1.

FIG. 2 illustrates an example of the receive-focusing process.

Here, FIG. 2 depicts the case of a linear probe in which the plurality of ultrasonic transducers of the probe 12 are arranged in a line in the horizontal direction in the diagram. The same concept may apply to a convex probe although it has a different probe shape.

Letting the width of each ultrasonic transducer in the azimuth direction be L, the distance from the central ultrasonic transducer in the azimuth direction to the n-th ultrasonic transducer toward the end position is given by nL.

It is assumed that, as illustrated in the same diagram, the reflection point of the ultrasonic wave is located at a distance (depth) d, which is vertical to the arrangement direction, from the central ultrasonic transducer. Then, the distance (length) $d_n$ between the n-th ultrasonic transducer and the reflection point is calculated in accordance with Equation (1).

$$d_n = ((nL)^2 + d^2)^{1/2} \quad (1)$$

Thus, the time $t_n$ taken for the ultrasonic echo from the reflection point to arrive at (to be received by) the n-th ultrasonic transducer is calculated in accordance with Equation (2) by using the sound velocity (ambient sound velocity) Va of the ultrasonic wave in the subject.

$$t_n = d_n/Va = ((nL)^2 + d^2)^{1/2}/Va \quad (2)$$

As described above, the distances between the ultrasonic transducers and the reflection point differ from one ultrasonic transducer to another. In this example, therefore, as illustrated in the graph at the top of the diagram, the closer the ultrasonic transducer to the end position in the arrangement direction, the longer the arrival time $t_n$ of the ultrasonic echo.

Specifically, if the time taken for the ultrasonic wave from the reflection point to be received by the central ultrasonic transducer is denoted by $t_1$, the ultrasonic wave received by the n-th ultrasonic transducer is delayed by the time $\Delta t = t_n - t_1$ with respect to the ultrasonic wave received by the central ultrasonic transducer. In this example, the delay time $\Delta t$ corresponds to a receive delay pattern.

The phasing addition unit 38 executes phasing addition on the signals corresponding to the respective ultrasonic transducers by using the delay times represented by the time $\Delta t$ described above to perform a receive-focusing process, and generates reception data.

The detection processing unit 40 corrects the reception data generated by the phasing addition unit 38 for attenuation caused by the distance in accordance with the depth of the reflection position of the ultrasonic wave, and then performs envelope detection processing to generate B-mode image data that is tomographic image information (brightness image information) in the subject.

The DSC (digital scan converter) 42 converts (raster-converts) the B-mode image data generated by the detection processing unit 40 into image data that supports a normal television signal scanning system.

The image processing unit 44 performs various kinds of necessary image processing, such as gradation processing, on the B-mode image data input from the DSC 42 to produce B-mode image data for display. The image processing unit 44 outputs the B-mode image data subjected to the image processing to the display control unit 26 for display and/or stores the B-mode image data subjected to the image processing in the image memory 46.

The image memory 46 is a well-known storage means (storage medium) that stores the B-mode image data processed by the image processing unit 44. The B-mode image data stored in the image memory 46 is read by the display control unit 26 for display on the display unit 28, as necessary.

The display control unit 26 causes the display unit 28 to display an ultrasound image by using the B-mode image data subjected to predetermined image processing by the image processing unit 44. If a region of interest ROI is set, the display control unit 26 causes the display unit 28 to also display the region of interest ROI, in addition to the ultrasound image, on the basis of the information on the region of interest ROI, which is supplied from the region-of-interest setting unit 21.

The display unit 28 includes, for example, a display device such as an LCD, and displays an ultrasound image under control of the display control unit 26. If a region of interest ROI is set, the display unit 28 displays the region of interest ROI overlaid on the ultrasound image.

The control unit 30 is a part that controls each component of the ultrasonic diagnostic apparatus 10 in accordance with instructions input by an operator through the operation unit 32.

Further, the control unit 30 supplies various kinds of information input by the operator by using the operation unit 32 to a necessary part. For example, if information necessary to set a region of interest ROI, which is used in the region-of-interest setting unit 21, information necessary to calculate a delay time, which is used in the element data processing unit 22 and the phasing addition unit 38 of the image generation unit 24, and information necessary for element data processing performed in the element data processing unit 22 are input to the operation unit 32, the control unit 30 supplies these pieces of information to the respective components, such as the transmitting unit 14, the receiving unit 16, the element data storage unit 20, the region-of-interest setting unit 21, the element data processing unit 22, the image generation unit 24, and the display control unit 26, as necessary.

The operation unit 32 is used by the operator to perform an input operation, and can be formed by a keyboard, a mouse, a trackball, a touch panel, or the like.

In addition, the operation unit 32 has an input function for allowing the operator to input various kinds of information, as necessary. For example, the operation unit 32 has an input function for inputting information on the probe 12 (the ultrasonic transducers), information related to the generation of processed element data, such as the transmit apertures and receive apertures in the probe 12 (the vibrator array 36), the number of pieces of element data to be superimposed, and the method for superimposing element data, the focal position of the ultrasonic beam, and so on. The operation unit 32 also has an input function for inputting information for placing a region of interest ROI.

The above input is made by, for example, the selection of a part to be imaged (a part to be diagnosed), the selection of image quality, the selection of the depth of the ultrasound image to be imaged, or the like.

The storage unit 34 is configured to store an operation program for allowing the control unit 30 to control each component of the ultrasonic diagnostic apparatus 10, transmit delay patterns, receive delay patterns, information related to the generation of processed element data, and information necessary for the control unit 30 to operate or control the ultrasonic diagnostic apparatus 10, which is input from the operation unit 32, such as information on the probe 12 and information on the transmit apertures, the receive apertures, and the focal position.

The storage unit 34 can be implemented using a well-known recording medium such as a hard disk, a flexible disk, an MO (Magneto-Optical disk), an MT (Masking Tape), a RAM (Random Access Memory), a CD-ROM, or a DVD-ROM.

Note that, in the ultrasonic diagnostic apparatus 10, the region-of-interest setting unit 21, the element data processing unit 22, the phasing addition unit 38, the detection processing unit 40, the DSC 42, the image processing unit 44, the display control unit 26, and so on are implemented by a CPU and an operation program for causing the CPU to perform various processing operations. In the present invention, however, these components may be implemented in digital circuitry.

As described above, the element data processing unit 22 is a part that superimposes, among the pieces of element data (unprocessed element data) stored in the element data storage unit 20, pieces of element data obtained by transmitting a predetermined number of (a plurality of) ultrasonic beams for which the ultrasonic transducers serving as the centers (central elements) are different and which have overlapping transmit areas, in accordance with the times at which the respective ultrasonic transducers perform reception and the positions of the ultrasonic transducers to generate processed element data.

Note that, in the following description, the ultrasonic transducers are also referred to simply as "elements".

Figure 3:
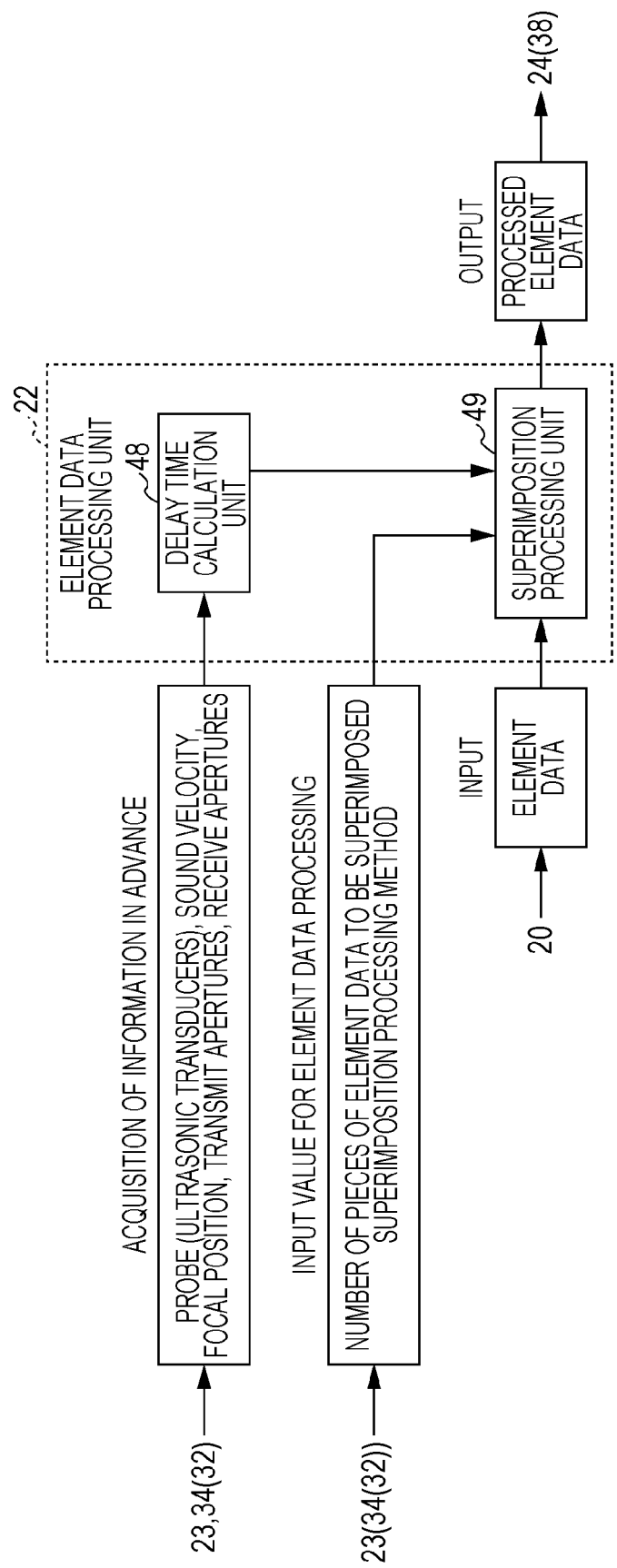
FIG. 3 is a block diagram conceptually illustrating an example of the configuration of an element data processing unit of the ultrasonic diagnostic apparatus illustrated in FIG. 1.

FIG. 3 conceptually illustrates in block diagram form the configuration of the element data processing unit 22.

As illustrated in FIG. 3, the element data processing unit 22 includes a delay time calculation unit 48 and a superimposition processing unit 49.

The delay time calculation unit 48 acquires, in advance, the information on the sound velocity, which is supplied from the processing condition changing unit 23, and information related to the probe 12 (the ultrasonic transducers (elements)), the focal position of the ultrasonic beam, the position of a sampling point (the output position of element data), the transmit apertures and receive apertures in the probe 12, and so on, which is input from the operation unit 32 or input from the operation unit 32 and stored in the storage unit 34.

Further, the delay time calculation unit 48 calculates the delay times of the ultrasonic echoes received by the elements in the receive apertures, that is, the delay times of the element data, on the basis of the geometric positions of the elements in the transmit apertures that oscillate ultrasonic waves to transmit (generate) an ultrasonic beam and the elements in the receive apertures that receive the ultrasonic echoes from the subject.

The delay time calculation unit 48 supplies information on the calculated delay times to the superimposition processing unit 49.

The superimposition processing unit 49 reads, from among the pieces of element data stored in the element data storage unit 20, pieces of element data to be subjected to superimposition (element data obtained by using ultrasonic beams for which the central elements are different and which have overlapping transmit areas (two or more pieces of element data generated for every two or more target regions)) on the basis of the information related to element data processing, such as the number of pieces of element data to be superimposed and the superimposition processing method, which is supplied from the processing condition changing unit 23, input from the operation unit 32, or input from the operation unit 32 and stored in the storage unit 34.

Further, the superimposition processing unit 49 superimposes the two or more pieces of element data in terms of reception time, that is, in such a manner that their times are aligned, and in such a manner that the received absolute positions of the elements of the probe unit are aligned, on the basis of the delay times corresponding to the respective pieces of element data, which are calculated by the delay time calculation unit 48, to generate processed element data.

The processing of element data, which is performed in the element data processing unit 22, will be described in detail hereinafter.

First, in a case where element data is obtained in the ultrasonic probe 12 by transmitting an ultrasonic beam to the subject from the transmit apertures, that is, elements (hereinafter referred to simply as transmit elements) that oscillate ultrasonic waves to transmit an ultrasonic beam, and by receiving an ultrasonic echo generated as a result of interaction with the subject by using the receive apertures, that is, elements (hereinafter referred to simply as receive elements) that receive ultrasonic echoes, the relationship between an ultrasonic beam from the transmit elements and element data obtained by the receive elements will be described.

Figure 4B:
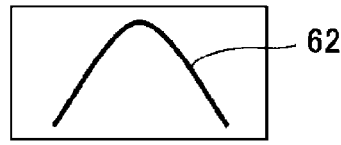
FIG. 4B and FIG. 4D are conceptual diagrams illustrating element data obtained by each transmission and reception of ultrasonic waves.
Figure 4D:
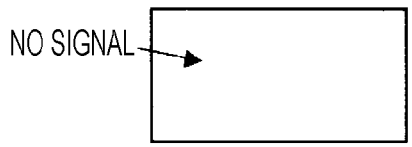
Figure 4A:
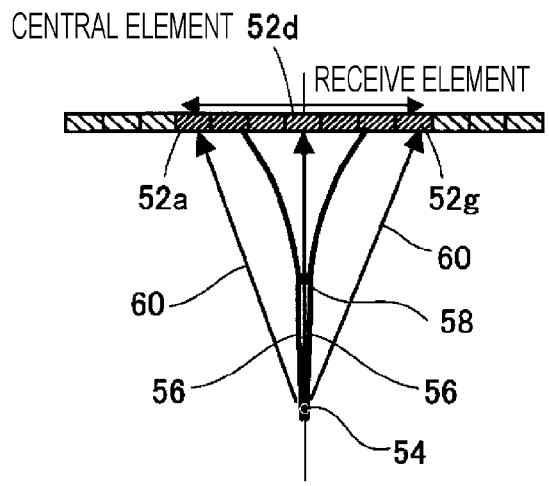
FIG. 4A and FIG. 4C are each a conceptual diagram for describing transmission and reception of ultrasonic waves by using an ideal ultrasonic beam.
Figure 4C:
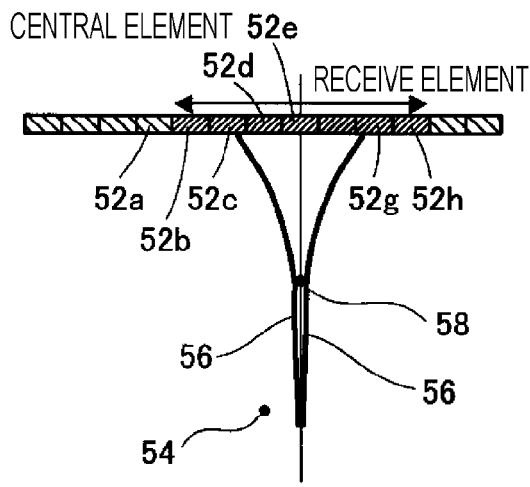

As an example, as illustrated in FIG. 4A, an ultrasonic beam is transmitted by using three elements 52c to 52e as transmit elements, and an ultrasonic echo is received by using seven elements 52a to 52g as receive elements. Then, as illustrated in FIG. 4C, the elements are moved (hereinafter also referred to as shifted) in the azimuth direction by one element so that an ultrasonic beam is transmitted by using three elements 52d to 52f as transmit elements and an ultrasonic echo is received by using seven elements 52b to 52h as receive elements. Accordingly, respective pieces of element data are acquired.

That is, the element 52d is the central element (the element serving as the center) in the example illustrated in FIG. 4A, and the element 52e is the central element in the example illustrated in FIG. 4C.

Consideration is now given to an ideal situation in which an ultrasonic beam 56 transmitted to a region under examination including a reflection point 54 converges at a focal point 58 and is narrowed down to a value equal to or less than the element spacing.

As in FIG. 4A, element data is acquired by transmitting the ultrasonic beam 56 from the elements 52c to 52e, which are the transmit elements, with the element 52d directly above the reflection point 54 (on a straight line connecting the reflection point and the focal point) being the central element, and by receiving an ultrasonic echo at the elements 52a to 52g, which are the receive elements, resulting in the focal point 58 of the ultrasonic beam 56 being located on a straight line connecting the element 52d, which is the central element, and the reflection point 54. In this case, the ultrasonic beam 56 is transmitted to the reflection point 54 and an ultrasonic echo reflected from the reflection point 54 is generated accordingly.

The ultrasonic echo from the reflection point 54 travels through a receive path 60 that extends over a predetermined angle and is received by the elements 52a to 52g, which are the receive elements, and element data 62, as illustrated in FIG. 4B, is obtained by the elements 52a to 52g. Note that, in FIG. 4B, the vertical axis represents time and the horizontal axis represents positions (the positions of the respective elements) in the azimuth direction, which match those in FIG. 4A (the same applies to FIG. 4D).

In contrast, as illustrated in FIG. 4C, when the central element is shifted by one element, the element 52e, which is adjacent to the element 52d directly above the reflection point 54, becomes the central element.

The ultrasonic beam 56 is transmitted from the elements 52d to 52f, which are the transmit elements, with the element 52e being the central element, and an ultrasonic echo is received by the elements 52b to 52h, which are the receive elements. At this time, if the ultrasonic beam 56 is also ideal, the reflection point 54 is not located in the transmit direction of the ultrasonic beam 56, that is, on a straight line connecting the central element 52e and the focal point 58. Thus, the ultrasonic beam 56 is not transmitted to the reflection point 54.

Accordingly, an ultrasonic echo reflected from the reflection point 54 is not generated, and the elements 52b to 52h, which are the receive elements, do not receive any ultrasonic echo from the reflection point 54. Thus, as illustrated in FIG. 4D, the element data does not include reflected signals from the reflection point (the element data has a signal intensity of "0").

Figure 5B:
FIG. 5B and FIG. 5D are conceptual diagrams illustrating element data obtained by each transmission and reception of ultrasonic waves.
Figure 5D:
Figure 5A:
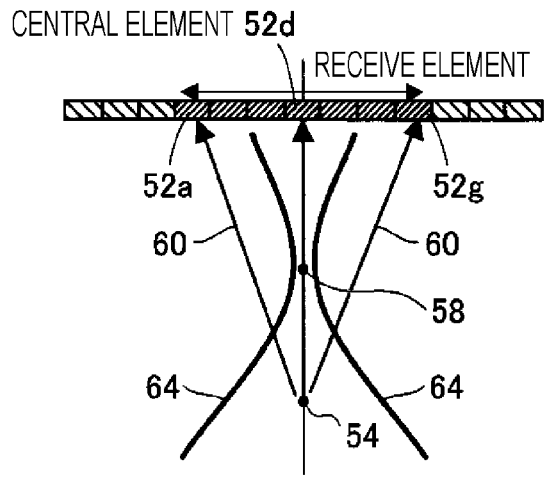
FIG. 5A and FIG. 5C are each a conceptual diagram for describing transmission and reception of ultrasonic waves by using an actual ultrasonic beam.
Figure 5C:
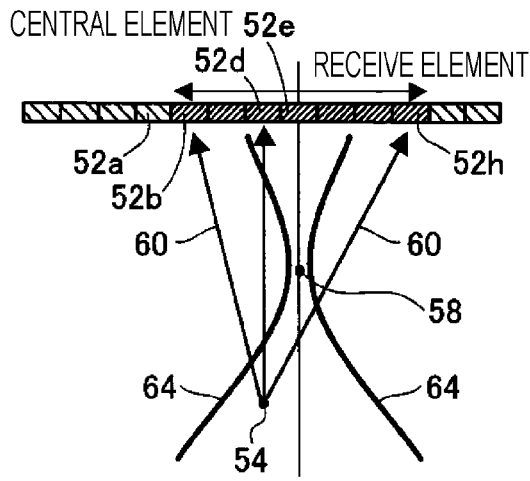

An actual ultrasonic beam, however, like an ultrasonic beam 64 illustrated in FIG. 5A and FIG. 5C, is diffused after converging at the focal point 58, and thus has a width larger than the element spacing.

Here, as in FIG. 5A, the ultrasonic beam 64 is transmitted in a manner similar to that in FIG. 4A by using the elements 52c to 52e as transmit elements with the element 52d directly above the reflection point 54 being the central element. In this case, even if the ultrasonic beam 64 is wide, the focal point 58 thereof is located on a straight line connecting the element 52d and the reflection point 54. Accordingly, the ultrasonic beam 64 is reflected at the reflection point 54 and an ultrasonic echo is generated.

As a result, in a manner similar to that in FIG. 4A, the ultrasonic echo from the reflection point 54 travels through a receive path 60 extending over a predetermined angle and is received by the elements 52a to 52g, which are the receive elements. In a similar manner, element data 66 (hereinafter also referred to as "true element data", for convenience) including a true signal, as illustrated in FIG. 5B, is obtained.

Then, as illustrated in FIG. 5C, the central element is shifted by one element, in a manner similar to that in FIG. 4C, so that the ultrasonic beam 64 is transmitted by using the elements 52d to 52f as transmit elements, with the adjacent element 52e being the central element, and an ultrasonic echo is received by using the elements 52b to 52h as receive elements. Also in this case, since the ultrasonic beam 64 is wide, the ultrasonic beam 64 is transmitted to (arrives at) the reflection point 54 if the reflection point 54 is not located in the transmit direction of the ultrasonic wave, that is, on a straight line connecting the element 52e, which is the central element, and the focal point 58.

Accordingly, an ultrasonic echo that would not be otherwise present, called a ghost reflected echo, emanates from the reflection point 54 in the transmit direction of the ultrasonic beam 64. As illustrated in FIG. 5C, the ghost reflected echo from the reflection point 54 travels through a receive path 60 extending over a predetermined angle and is received by the elements 52b to 52h, which are the receive elements. As a result, element data 68 (hereinafter referred to also as "ghost element data", for convenience) including a ghost signal, as illustrated in FIG. 5D, is obtained by the elements 52b to 52h.

The ghost element data 68 causes a reduction in the accuracy of an ultrasound image generated from element data.

The element data processing unit 22 is configured such that the delay time calculation unit 48 calculates a delay time for element data and the superimposition processing unit 49 superimposes two or more pieces of element data in accordance with the delay time and the absolute positions of the elements to generate processed element data that is accurate element data with a true signal enhanced and a ghost signal attenuated.

As described above, the delay time calculation unit 48 calculates a delay time for element data received by each of the elements of the receive elements (receive apertures).

Specifically, the propagation distance of the ultrasonic beam 64 illustrated in FIG. 5C is the sum of a transmit path along which the ultrasonic beam 64 from the element 52e, which is the central element, travels through the focal point 58 and reaches the reflection point 54 and a receive path along which the ghost reflected echo from the reflection point 54 reaches each of the elements 52b to 52h, which are the receive elements.

The propagation distance of the ultrasonic beam 64 illustrated in FIG. 5C is longer than the propagation distance of the ultrasonic beam 64 illustrated in FIG. 5A, that is, the sum of a transmit path along which the ultrasonic beam 64 from the central element 52d travels through the focal point 58 and reaches the reflection point 54 and a receive path along which the true ultrasonic echo from the reflection point 54 reaches the elements 52a to 52g, which are the receive elements.

For this reason, the ghost element data 68 as illustrated in FIG. 5D is delayed with respect to the true element data 66 as illustrated in FIG. 5B.

In the delay time calculation unit 48 of the element data processing unit 22, the time difference of the ghost element data with respect to the true element data, or the delay time, is calculated from the sound velocity and the geometric arrangement of the transmit elements, the focal point of the ultrasonic beam, the reflection point in the subject, and the receive elements.

Accordingly, the computation of the delay time requires information such as the shape of the probe 12 (such as the element spacing and linear or convex), the sound velocity, the position of the focal point, the transmit apertures, and the receive apertures. The delay time calculation unit 48 acquires these pieces of information, which are input by using the operation unit 32 or stored in the storage unit 34, and computes the delay time.

Note that the sound velocity may have a fixed value (for example, 1540 m/sec), or, if a sound velocity calculation unit is included, a sound velocity (ambient sound velocity) calculated by the sound velocity calculation unit may be used. Alternatively, an operator may be able to input a sound velocity.

Here, as described above, if the processing condition changing unit 23 changes the value of the sound velocity, the delay time calculation unit 48 calculates a delay time by using the value of the sound velocity set by the processing condition changing unit 23.

The delay time can be calculated from the difference in the propagation time calculated from the sound velocity and the total length (propagation distance) of a transmit path along which an ultrasonic beam from transmit elements travels through a focal point and reaches a reflection point and a receive path along which a true reflected ultrasonic echo or a ghost reflected signal from the reflection point reaches receive elements, the total length (propagation distance) being calculated from the geometric arrangement of the transmit elements, the focal point of the ultrasonic beam, the reflection point in the subject, and the receive elements, for example.

Figure 6A:
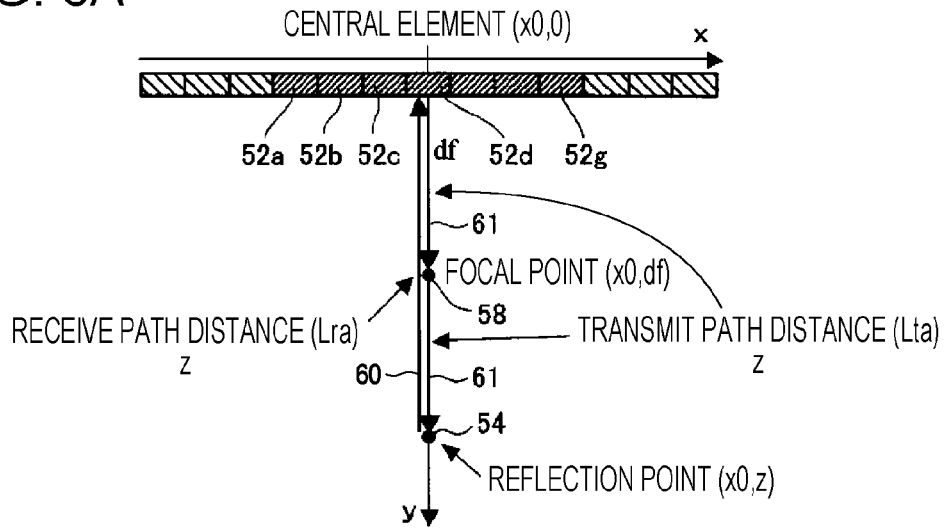
FIG. 6A and FIG. 6B are conceptual diagrams for describing a path of a sound wave in a case where the transmission and reception of ultrasonic waves are performed by different central elements with respect to the same reflection point.
Figure 6B:
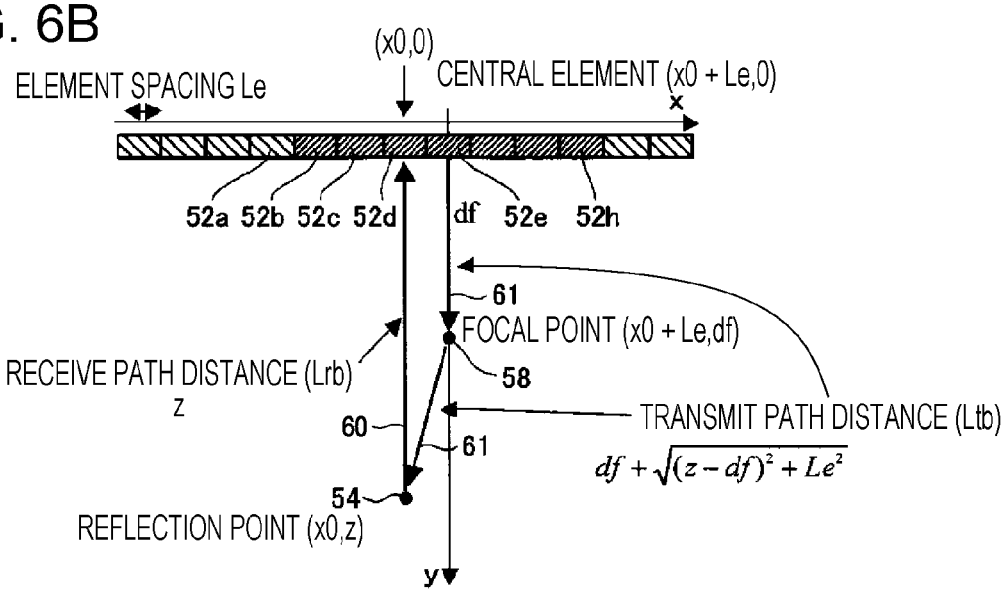

In the present invention, the length of the transmit path and receive path of an ultrasonic beam in the case of a true ultrasonic echo and a ghost reflected echo can be determined in a way illustrated in FIG. 6A and FIG. 6B, for example. Note that, in FIG. 6A and FIG. 6B, the x direction represents the azimuth direction and the y direction represents the depth direction.

In addition, FIG. 6A depicts the transmission and reception of ultrasonic waves which is performed in a manner similar to that in FIG. 5A, and FIG. 6B depicts the transmission and reception of ultrasonic waves which is performed in a manner similar to that in FIG. 5C.

In the case of a true ultrasonic echo, as illustrated in FIG. 6A (FIG. 5A), the element 52d, which is the central element, the focal point 58, and the reflection point 54 are positioned on a straight line (the positions thereof in the azimuth direction coincide with one another). That is, the focal point 58 and the reflection point 54 are located directly below the central element 52d.

Thus, assuming that the position of the element 52d, which is the central element, is given by the coordinates (x0, 0) on the two-dimensional x-y coordinate system, the x coordinates of both the focal point 58 and the reflection point 54 are also given by "x0". In the following, the position of the focal point 58 in this transmission is given by the coordinates (x0, df), the position of the reflection point 54 is given by the coordinates (x0, z), and the spacing of each element is denoted by Le.

In this case, the length (transmit path distance) Lta of a transmit path 61 of an ultrasonic beam from the element 52d, which is the central element, that travels through the focal point 58 and reaches the reflection point 54, and the length (receive path distance) Lra of a receive path 60 of a true reflected ultrasonic echo from the reflection point 54 that reaches the element 52d can be calculated by Lta=Lra=z.

In the case of a true ultrasonic echo, therefore, an ultrasonic echo propagation distance Lua is given by Lua=Lta+Lra=2z.

Then, as illustrated in FIG. 6B, the transmit elements and the receive elements are shifted by one element in the x direction (azimuth direction) (shifted rightward in the diagram) so that transmission and reception are performed with the element 52e being the central element. In this case, as illustrated in FIG. 5C, a ghost reflected echo is reflected at the reflection point 54.

The reflection point 54 is located directly below the element 52d (at the same position in the azimuth direction). Therefore, as illustrated in FIG. 6B, in this transmission and reception, the positions of the element 52e, which is the central element, and the reflection point 54 in the x direction are displaced from each other by one element, that is, by Le, in the x direction.

Since the coordinates of the element 52d whose position in the x direction coincides with that of the reflection point 54 are (x0, 0), the coordinates of the element 52e, which is the central element, are (x0+Le, 0) and the coordinates of the focal point 58 in this transmission are (x0+Le, df). Note that the coordinates of the reflection point 54 are (x0, z), as described above.

Accordingly, the length (transmit path distance) Ltb of a transmit path 61 of an ultrasonic beam from the element 52e, which is the central element, that travels through the focal point 58 and reaches the reflection point 54 can be calculated by $Ltb=df+\sqrt{\{(z-df)^2+Le^2\}}$. On the other hand, the length (receive path distance) Lrb of a receive path 60 of a ghost reflected signal from the reflection point 54 that reaches the element 52d directly thereabove (at the same position in the x direction=the azimuth direction) can be calculated by $Lrb=z$.

Thus, an ultrasonic wave propagation distance Lub in the case of a ghost reflected echo is given by $Lub=Ltb+Lrb=df+\sqrt{\{(z-df)^2+Le^2\}}+z$.

In this manner, a value obtained by dividing the ultrasonic wave propagation distance Lua determined from the geometric arrangement illustrated in FIG. 6A, which is the sum of the distance Lta of the transmit path 61 and the distance Lra of the receive path 60, by the sound velocity corresponds to the true ultrasonic echo propagation time. Further, a value obtained by dividing the ultrasonic wave propagation distance Lub determined from the geometric arrangement illustrated in FIG. 6B, which is the sum of the distance Ltb of the transmit path 61 and the distance Lrb of the receive path 60, by the sound velocity corresponds to the ghost reflected echo propagation time.

The delay time is determined from the difference between the true ultrasonic echo propagation time obtained when the x coordinates of the reflection point 54 and the central element coincide with each other and the ghost reflected echo propagation time obtained when the x coordinates of the reflection point 54 and the central element are displaced from each other by the spacing of one element.

Note that the geometric models in FIG. 6A and FIG. 6B are models in which the transmit path 61 passes through the focal point 58; however, the present invention is not limited thereto. For example, a path which directly reaches the reflection point 54 without passing through the focal point 58 may be used.

In addition, the geometric models in FIG. 6A and FIG. 6B are based on, but are not limited to, the case of a linear probe. Any other probe may also be used to perform similar geometric computation in accordance with the shape of the probe.

For example, in the case of a convex probe, a geometric model can be set from the radius of the probe and the angle defined by the element spacing and computation can be performed in a similar way.

Furthermore, in the case of steer transmission, a geometric model that takes into account information such as transmit angle can be used, and the delay times of true element data and neighboring ghost element data can be calculated based on the positional relationship between the transmit elements and the reflection point.

Moreover, instead of a method of calculating a delay time by using a geometric model, the following method may be used. A delay time is determined in advance for each measurement condition from measurement results obtained by measuring a high-brightness reflection point in accordance with the measurement conditions of the apparatus, and is stored in the apparatus to allow the delay time for the same measurement condition to be read.

Alternatively, if a delay time is changed by the processing condition changing unit 23, the delay time to be used may be set on the basis of delay time information supplied from the processing condition changing unit 23.

Figure 6C:
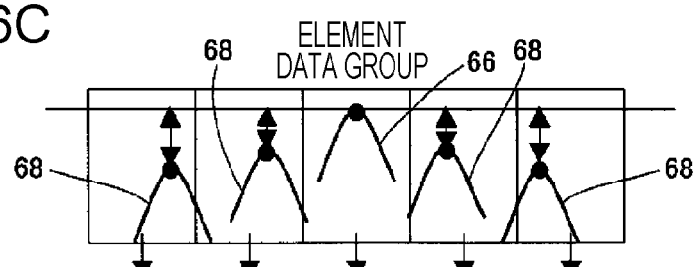
FIG. 6C is a conceptual diagram for describing pieces of element data obtained by a plurality of elements.

FIG. 6C illustrates the true element data 66 and the ghost element data 68.

In FIG. 6C, the true element data 66, that is, element data obtained by transmission and reception with the central element and the reflection point 54 whose positions in the x direction coincide (in the illustrated example, element data obtained when the element 52d is the central element), is illustrated in the center in the azimuth direction. Further, depicted on either side of the center is ghost element data, that is, element data obtained by transmission and reception with the central element and the reflection point 54 whose positions in the x direction do not coincide (in the illustrated example, element data obtained when the element 52c, the element 52e, or the like is the central element).

Figure 6D:
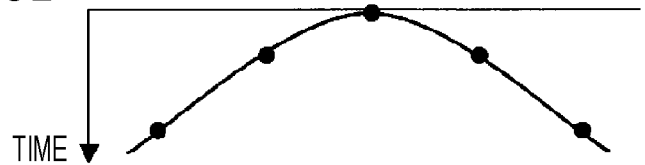
FIG. 6D is a conceptual diagram for describing delay times of the pieces of element data illustrated in FIG. 6C.

Further, FIG. 6D illustrates an example of the delay times of the ghost element data 68 with respect to the true element data 66, which are obtained from the geometric computation described above. The illustration shows that the pieces of element data 68 of the ghost signals are symmetrically delayed in time with respect to the true element data 66 in the x direction, that is, in the azimuth direction.

Note that the delay times calculated by the delay time calculation unit 48 of the element data processing unit 22 in the way described above can also be used for delay correction performed in the phasing addition unit 38.

Though described below in detail, in the invention, element data obtained by transmission of an ultrasound beam, for which the central element is different and at least a part of the ultrasound beam overlaps, is superimposed on element data obtained by transmission with a certain element of interest as a central element (transmission and reception of an element of interest) according to the reception time of the ultrasonic echo and the position of the element to generate processed element data (second element data) of the element of interest (to reconstruct element data of the element of interest).

In FIG. 6A, the reflection point 54 represents the position of a certain sampling point (the output position of the element data) positioned directly below the element of interest (at the same position in the azimuth direction/on a straight line connecting the element of interest and the focal point). In the present invention, a transmit/receive path to/from a sampling point in transmission and reception for the element of interest is regarded as a transmit/receive path of true element data and a transmit/receive path to/from the same sampling point in the transmission and reception of ultrasonic waves for which a different central element is used (transmission and reception from a neighboring element) is regarded as a transmit/receive path of ghost element data. A delay time is calculated by using the difference between both transmit paths, and is used for superimposition of element data in such a manner that their times are aligned. In other words, a delay time is calculated, assuming that element data obtained by transmission and reception for the element of interest is true element data and element data obtained by transmission and reception for a different central element is ghost element data, and the pieces of element data are superimposed.

In the present invention, a similar concept is used to calculate delay times for all the sampling points (the output positions of all the pieces of element data) for superimposition of element data, and processed element data of each element is generated.

Here, actually, the length of the receive path (the receive path distance Lrb) does not change even if the position of the sampling point (reflection point) is shifted in the azimuth direction (x direction). It is therefore sufficient to calculate a delay time for each element of interest with respect to element data obtained by transmission and reception for a different central element at each sampling point in the depth direction (y direction).

In this superimposition processing, furthermore, it is not necessary to know which element data is true element data. That is, as described in detail below using parts (a) to (h) of FIG. 7, in this superimposition processing, a signal included in element data is automatically enhanced and remains if the signal is a true signal, and is canceled if the signal is a ghost signal. That is, if a reflection point is located on the line of the element of interest, a signal from the reflection point is enhanced since the processes based on the delay times match, whereas a signal from a reflection point on a line other than the line of the element of interest is canceled since the processes based on the delay times do not match.

Then, the superimposition processing unit 49 of the element data processing unit 22 of the present invention performs superimposition processing on the element data by using the delay time calculated by the delay time calculation unit 48 in the way described above.

Note that the superimposition processing performed in the superimposition processing unit 49 requires information on the number of pieces of element data to be superimposed and the superimposition processing method. These pieces of information may be input by using the operation unit 32 in advance or stored in the storage unit 34 in advance. In addition, as described above, if the processing condition changing unit 23 changes the number of superimpositions and/or the apodization factor (weighting factor), the superimposition processing unit 49 performs superimposition processing on the basis of the information supplied from the processing condition changing unit 23.

Parts (a) to (h) of FIG. 7 illustrate an example of the superimposition processing performed in the superimposition processing unit 49. Note that the example illustrated in parts (a) to (h) of FIG. 7 depicts the case where the number of pieces of element data is five and the number of pieces of element data to be superimposed is three.

In part (a) of FIG. 7, five pieces of element data obtained by five transmissions and receptions of ultrasonic waves are displayed side by side. Part (a) of FIG. 7 further depicts transmission of an ultrasonic beam and reception of ultrasonic echoes for each piece of element data. The horizontal axis of the plot of each piece of element data represents receive elements that are depicted centered on the central element in the transmission and reception of ultrasonic beams for each piece of element data. The vertical axis represents reception time. In this example, transmission and reception of ultrasonic waves are performed five times with the central element shifted one by one, for example, the elements 52b to 52f.

Part (a) of FIG. 7 illustrates a state in which a single reflection point is located only directly below the central element in the element data depicted at the center. That is, in the element data in the middle of the five pieces of element data, a true ultrasonic echo from the reflection point is received in the transmission and reception of the ultrasonic wave. That is, the element data in the middle is true element data.

For the two pieces of element data on either side other than the element data in the middle, the reflection point is not located directly below the central elements in the transmission and reception of ultrasonic waves. However, due to the spread of the transmitted ultrasonic beams, element data of reflected echoes produced by the ultrasonic beams impinging on the reflection point located directly below the transmit element for the element data in the middle, that is, ghost element data, appears.

The farther the ghost element data from the true element data, the longer the ultrasonic wave propagation time to the reflection point. Thus, the reception time of the ghost element data is later than that of the true element data. In addition, the receive element that is first to receive the ultrasonic echo from the reflection point is an element located immediately above the reflection point (an element whose position in the azimuth direction coincides with that of the reflection point).

Here, the horizontal axis of the plot of each piece of element data in part (a) of FIG. 7 is centered on the central element in the transmission of an ultrasonic beam. In the example illustrated in part (a) of FIG. 7, therefore, since transmission is performed with the central element shifted by one element for each piece of element data, the absolute positions of the respective elements in the azimuth direction are shifted by one element for each piece of element data. Specifically, for the element data in the middle, the receive element that is first to receive a reflected signal from the reflection point is the central element, whereas, for the element data on either side of the element data in the middle, this receive element is shifted by one element with respect to that for the element data in the middle in such a manner that, for the element data on the right side, this receive element is shifted to the left by one element and, for the element data on the left side, this receive element is shifted to the right by one element. For the element data on either end, furthermore, this receive element is shifted by two elements with respect to that for the element data in the middle in such a manner that, for the element data at the right end, this receive element is shifted to the left by two elements and, for the element data at the left end, this receive element is shifted to the right by two elements. In this manner, for the ghost signals, in addition to the reception times being delayed with respect to that of the true signal, the receive elements are also shifted in the direction thereof.

Part (b) of FIG. 7 illustrates an example of the delay times regarding the reception times with respect to the reception time of the element data in the middle of the five pieces of element data illustrated in part (a) of FIG. 7.

By using the delay times illustrated in part (b) of FIG. 7, the superimposition processing unit 49 performs delay-time correction on a number of pieces of element data to be superimposed, e.g., three pieces of element data in the illustrated example, centered on the element data of an element of interest, where the element of interest is the central element for the element data in the middle. In addition, the superimposition processing unit 49 superimposes the pieces of unprocessed element data for the three pieces of element data with each piece of element data shifted in accordance with the difference between the position of the corresponding element and the position of the element of interest (the difference in position between the central elements), e.g., with the element data on either side shifted by one element in the azimuth direction in the illustrated example, that is, with their phases aligned, to determine a piece of superimposition-processed element data for the element of interest.

That is, this example involves superimposing, on element data obtained by transmission and reception of ultrasonic waves with the element of interest being the central element (hereinafter also referred to as the element data for the element of interest), element data obtained by transmission and reception of ultrasonic waves with an element adjacent to the element of interest being the central element (hereinafter also referred to as the element data for the adjacent element) to generate processed element data of the element data for the element of interest.

Part (c) of FIG. 7 illustrates the superimposition-processed element data for the element of interest obtained in the way described above.

As described above, the element data for the element of interest illustrated in part (a) of FIG. 7 is true element data for which the reflection point is located directly below the central element (i.e., the element of interest). In addition, element data obtained by transmission and reception for which an element adjacent to the element of interest is the central element is also data of an ultrasonic echo reflected from the reflection point to which the ultrasonic beam is incident.

Accordingly, the element data for the adjacent element on either side of the element data for the element of interest is subjected to delay-time correction and to a shift in the azimuth direction to perform phase alignment. In consequence, as illustrated in part (c) of FIG. 7, the pieces of element data for the adjacent elements and the element data for the element of interest are superimposed at a high-brightness position since their phases are aligned. Therefore, for example, these pieces of element data are summed, resulting in the element data value being a large value (high-brightness value). For example, the pieces of element data are averaged to obtain an average value which is also an enhanced value (high-brightness value).

In contrast, part (d) of FIG. 7 illustrates an example of the case in which, while the same element data as that in part (a) of FIG. 7 is used, the element of interest is the central element for the element data that is left-adjacent to the element data in the middle. That is, this example is an example of the case in which, in the transmission and reception of ultrasonic waves with the central element being an element directly below which the reflection point is not located, the central element is the element of interest. Thus, element data for which this element is the central element is ghost element data.

Part (e) of FIG. 7 corresponds to part (b) of FIG. 7, and illustrates an example of the delay times regarding the reception times of the five pieces of element data illustrated in part (d) of FIG. 7 with respect to the reception time of the element data for the element of interest. That is, since parts (a) and (d) of FIG. 7 illustrate the same element data, the illustrated delay times are also the same as the delay times regarding the reception times of the five pieces of element data illustrated in part (a) of FIG. 7 with respect to the reception time of the element data in the middle.

The superimposition processing unit 49 performs delay-time correction on a number of pieces of element data to be superimposed, e.g., three pieces of element data in the illustrated example, centered on the element data for the element of interest by using the delay times illustrated in part (e) of FIG. 7 (i.e., the same as those in part (b) of FIG. 7). In addition, the superimposition processing unit 49 superimposes the pieces of unprocessed element data for the three pieces of element data with each piece of element data shifted in accordance with the difference between the position of the corresponding element and the position of the element of interest (the difference in position between the central elements), e.g., with the element data on either side shifted by one element in the azimuth direction in the illustrated example, to determine a piece of superimposition-processed element data for the element of interest.

Part (f) of FIG. 7 illustrates the superimposition-processed element data for the element of interest obtained in the way described above.

The element data for the element of interest illustrated in part (d) of FIG. 7 is ghost element data. Thus, even if unprocessed element data for the adjacent element on either side of the element data for the element of interest is subjected to delay-time correction and to a shift in the azimuth direction to perform phase alignment, as illustrated in part (f) of FIG. 7, the pieces of element data for the adjacent elements and the element data for the element of interest are not superimposed since their phases are not aligned. Therefore, for example, if these three pieces of element data are summed, the resulting sum value is not large because the phases of the pieces of element data are not aligned and phase-inverted signals would cancel each other out, for example. For example, the pieces of element data are averaged to obtain an average value which is a small value.

Part (g) of FIG. 7 illustrates the states of superimposed three pieces of adjacent element data for the five pieces of element data in the illustrated example as a result of also subjecting each of the other pieces of element data to similar delay-time correction and to a shift in the azimuth direction as element data for the element of interest. Part (h) of FIG. 7 illustrates the result of subjecting these pieces of element data to superimposition processing, namely, summing processing or averaging processing, for example.

As illustrated in part (h) of FIG. 7, when a central element directly below which the reflection point is located, as illustrated in part (a) of FIG. 7, is used as an element of interest, element data of a true signal is determined as superimposition-processed element data having high-brightness values. In two pieces of element data on either side, or four pieces of element data in total, on the other hand, the sum or average of pieces of element data whose phases are not aligned with each other is taken for ghost element data. This allows the pieces of element data to cancel each other out, resulting in the ghost superimposition-processed element data having values that are smaller than those of the superimposition-processed element data having high-brightness values, which is the element data of the true signal. The influence of the ghost element data on the true element data can be reduced or can be small to be negligible.

That is, superimposing, on element data obtained by transmission of an ultrasonic beam with an element of interest being the central element (element data for the element of interest), where the element of interest is a certain element, one or more pieces of element data obtained by transmission and reception of ultrasonic waves for which a different central element is used and for which a transmission region of the ultrasound beam overlaps in such a manner that the times and the positions in the azimuth direction are aligned to generate processed element data corresponding to the element data for the element of interest (in other words, to reconstruct (correct) the element data for the element of interest by using element data obtained by transmission and reception of an ultrasonic beam at least part of which overlaps that for the element of interest and for which a different central element is used) can increase the brightness of true element data and can reduce ghost element data.

Accordingly, processed element data is subjected to phasing addition or detection processing to generate reception data to generate an ultrasound image. This enables an ultrasound image to be generated from element data which is free of influence of ghosting and for which it is equivalent to saying that every point on a sound ray is brought into focus. Thus, a high-brightness, high-quality ultrasound image with good sharpness can be generated.

Note that, in the following description, the generation of processed element data is also referred to as multi-line processing.

In the present invention, the term central element refers to the element at the center in the azimuth direction when the number of apertures for transmission (the number of elements that transmit ultrasonic waves) is an odd number.

On the other hand, when the number of apertures is an even number, any one of the elements located in the center in the azimuth direction is used as the central element or an element assumed to be located in the middle in the azimuth direction is used as the central element. That is, when the number of apertures is an even number, computation may be performed assuming that the focal point is located on a line in the middle of the apertures.

Note that the superimposition processing method in the superimposition processing unit 49 may involve taking an average value or a median value, as well as simply performing summation, or performing summation after multiplication with a coefficient. Note that while taking an average value or a median value may be considered to be equivalent to applying an averaging filter or a median filter in the element data level, an inverse filter or any other filter used in typical image processing may be applied instead of an averaging filter or a median filter.

The above disclosure is not intended to be limiting. Alternatively, the superimposition processing may be changed on the basis of the respective feature values of the pieces of element data to be superimposed. For instance, the pieces of element data to be superimposed may be compared, and a maximum value may be taken when they are similar, an average value may be taken when they are not similar, or an intermediate value may be taken when there is a biased distribution.

In addition, the number of pieces of element data to be superimposed on the element data for the element of interest is not limited to two, as in illustrated example, and may be one or more than two. That is, the number of pieces of element data to be superimposed on the element data for the element of interest may be set, as appropriate, in accordance with the required processing speed (such as the frame rate), image quality, and so on. Basically, the larger the number of pieces of element data to be superimposed, the more the image quality improved.

Here, it is desirable that the number of pieces of element data to be superimposed on the element data for the element of interest be determined in accordance with the degree of the spread of the beam width of the ultrasonic beam. Accordingly, when the beam width varies depending on the depth, the number of pieces of element data to be superimposed may also be changed depending on the depth.

In addition, since the beam width depends on the number of transmit apertures, the number of pieces of element data to be superimposed may be changed in accordance with the number of transmit apertures. Alternatively, the number of pieces of element data to be superimposed may be changed on the basis of a feature value such as a luminance value of an image, or an optimum number of pieces of element data to be superimposed may be selected from images created by changing the number of pieces of element data to be superimposed in accordance with a plurality of patterns.

In addition, the processed element data generated through superimposition does not need to correspond to any one of the pieces of unprocessed element data to be used for superimposition. That is, generated processed element data may be data corresponding to a position (line) different from that for the unprocessed element data.

For example, processed element data corresponding to a line at the intermediate position of the lines corresponding to the respective pieces of unprocessed element data may be generated.

In addition, the number of lines for which processed element data is generated may be equal to or larger or smaller than the number of lines for which unprocessed element data has been acquired (the number of lines on which transmission and reception of ultrasonic waves have been performed).

Specifically, for example, processed reception data corresponding to lines for which unprocessed element data has been acquired and a line at the intermediate position of the lines may be generated to generate processed reception data corresponding to lines, the number of which is twice as large as the number of lines on which transmission and reception of ultrasonic waves have been performed.

Note that, in the foregoing multi-line processing, pieces of element data obtained by transmission of a plurality of ultrasonic beams for which the central elements are different and whose transmit directions are parallel (whose angles are identical) are superimposed to generate processed element data of element data for an element of interest; however, the present invention is not limited thereto.

For example, pieces of element data obtained by transmission of a plurality of ultrasonic beams for which the central elements are identical and whose transmit directions (angles) are different may be superimposed to generate processed element data. In this case, which ultrasonic beam is transmitted to obtain processed element data of element data to be generated (that is, in which direction of sound ray to generate processed element data) may be set by default in accordance with the part to be diagnosed, the type of the probe, or the like, or may be selected by an operator.

Alternatively, element data obtained by transmission of parallel ultrasonic beams for which the central elements are different and element data obtained by transmission of ultrasonic beams for which the central elements are identical and whose transmit directions are different may be both used to generate processed element data.

As described above, the element data processing unit 22 delivers the generated processed element data to the image generation unit 24 (the phasing addition unit 38).

In the image generation unit 24 to which the processed element data is supplied, as described above, the phasing addition unit 38 executes phasing addition on the processed element data to perform a receive-focusing process and generates reception data, and the detection processing unit 40 performs attenuation correction and envelope detection processing on the reception data to generate B-mode image data.

In the image generation unit 24, furthermore, the DSC 42 raster-converts the B-mode image data into image data that supports a normal television signal scanning system, and the image processing unit 44 performs predetermined processing such as gradation processing.

The image processing unit 44 stores the generated B-mode image data in the image memory 46, and/or delivers it to the display control unit 26 to display a B-mode image of the subject on the display unit 28.

Here, as described above, if a region of interest is set by the region-of-interest setting unit 21, the processing condition changing unit 23 changes a processing condition for multi-line processing in the element data processing unit 22 on the basis of information on the set region of interest, and the element data processing unit 22 performs multi-line processing on the basis of set processing conditions.

Specifically, for example, the number of superimpositions in multi-line processing within the region of interest ROI is set different from that within the region other than the region of interest ROI.

An example of the processing condition changing method performed by the processing condition changing unit 23 will be described in detail with reference to FIG. 8A and FIG. 8B.

FIG. 8A is a conceptual diagram for describing ranges of sum lines (the numbers of superimpositions) before and after the setting of a region of interest ROI.

FIG. 8A illustrates an imaging area, in which the horizontal direction corresponds to the arrangement direction of elements and the vertical direction corresponds to the depth direction.

First, before the setting of a region of interest ROI, multi-line processing is performed on the entire imaging area under predetermined conditions to generate an ultrasound image. For example, when multi-line processing is performed on a line of interest represented by the one-dot chain line in the diagram, the number of superimpositions for multi-line processing is assumed to be equal to the number of lines within a range represented by the broken line.

In contrast, when a region of interest ROI represented by the solid line in the diagram is set, for the line of interest (sampling point) within the region of interest ROI, the number of lines within a range represented by the thick line is used as the number of lines for multi-line processing and is set larger than the number of superimpositions before the setting of the region of interest ROI. For example, if the range of lines to be superimposed in the multi-line processing before the setting of the region of interest ROI is smaller than the width of an ultrasonic beam, the number of lines to be superimposed in the multi-line processing after the setting of the region of interest ROI is set in accordance with the width of the ultrasonic beam.

In this case, for the region other than the region of interest ROI, the number of superimpositions for multi-line processing is the same as the number of superimpositions before the setting of the region of interest ROI.

FIG. 8B is a conceptual diagram for describing another example of ranges of sum lines (the number of superimpositions) before and after the setting of a region of interest ROI.

FIG. 8B illustrates an imaging area, in which the horizontal direction corresponds to the arrangement direction of elements and the vertical direction corresponds to the depth direction.

First, before the setting of a region of interest ROI, the number of superimpositions for multi-line processing is set to be equal to the number of lines within a range represented by the broken line in the diagram in accordance with the depth of a sampling point so as to correspond to the width of an ultrasonic beam.

In contrast, when a region of interest ROI represented by the solid line in the diagram is set, for the line of interest (sampling point) within the region of interest ROI, the number of lines within a range represented by the thick line is used as the number of lines for multi-line processing to perform multi-line processing in a manner similar to that before the setting of the region of interest ROI. For the region other than the region of interest ROI, on the other hand, no multi-line processing is performed and an ultrasound image is generated from unprocessed element data.

Specifically, in the example illustrated in FIG. 8A, when a region of interest ROI is set, the processing condition changing unit 23 sets the number of superimpositions for multi-line processing within the region other than the region of interest ROI to the same value as that before the setting of the region of interest ROI (without any change), and sets the number of superimpositions for multi-line processing within the region of interest ROI to be larger than the number of superimpositions within the region other than the region of interest ROI.

This enables high-accuracy multi-line processing within the region of interest ROI, resulting in an improvement in the image quality of the region of interest ROI. In addition, a reduction in the computational load for the region other than the region of interest ROI can be achieved, preventing a reduction in frame rate.

Note that the number of superimpositions within the region other than the region of interest ROI after the setting of the region of interest ROI may be smaller than that before the setting of the region of interest ROI. For example, the number of superimpositions for the region other than the region of interest ROI may be set to maintain consistency in the total number of superimpositions in within one frame. This can favorably prevent a reduction in frame rate.

Note that, in the present invention, the processing condition changing method performed by the processing condition changing unit 23 is not limited to the configuration described above in which the number of superimpositions for multi-line processing within the region of interest ROI is set larger.

For example, as in the example illustrated in FIG. 8B, when a region of interest ROI is set, the processing condition changing unit 23 may set the number of superimpositions within the region of interest ROI to be equal to that before the setting of the region of interest ROI, and set the number of superimpositions within the region other than the region of interest ROI to be smaller than that before the setting of the region of interest ROI.

Alternatively, when a region of interest ROI is set, the processing condition changing unit 23 may (set the number of superimpositions to 1 to) prevent multi-line processing from being performed in the region other than the region of interest ROI. That is, in the region other than the region of interest ROI, an ultrasound image may be generated from unprocessed element data.

Alternatively, a configuration may be used in which an image of only the region of interest ROI is displayed while nothing is displayed for the region other than the region of interest ROI. An image obtained immediately before the region of interest ROI is set may be displayed.

In another configuration in which, when a region of interest ROI is not set, no multi-line processing is performed (by setting the number of superimpositions to 1) and an ultrasound image is generated from unprocessed element data, when a region of interest ROI is set, the processing condition changing unit 23 may set the number of superimpositions within the region of interest ROI to 2 or more to perform multi-line processing.

The configurations described above allow high-accuracy multi-line processing within the region of interest ROI, and also allow a reduction in the computational load for the region other than the region of interest ROI. Accordingly, the image quality of the region of interest ROI can be improved and a reduction in frame rate can be prevented.

In the present invention, furthermore, a processing condition that is changed by the processing condition changing unit 23 is not limited to the number of superimpositions in multi-line processing.

For example, the processing condition changing unit 23 may be configured to change a weighting factor (apodization factor) for superimposition processing performed in the superimposition processing unit 49, in accordance with the set region of interest ROI. For example, the apodization factor may be set in accordance with the width of the region of interest ROI.

Changing an apodization condition to a value appropriate to the region of interest ROI can achieve more preferable effect of superimposition of unprocessed element data within the region of interest ROI, achieving improved quality of an ultrasound image to be generated from processed element data after multi-line processing.

Alternatively, the processing condition changing unit 23 may set the sound velocity from which the delay time calculation unit 48 calculates a delay time, or the delay time itself in accordance with the position of the region of interest ROI to set the sound velocity or delay time at that position.

In a living body, sound velocity differs depending on the part such as muscle or fat. This causes the delay time to differ depending on the part to be focused on. Superimposition without the use of an appropriate delay time may make it difficult to carry out appropriate superimposition, resulting in a concern that sufficient image quality might not be achievable.

In contrast, setting a sound velocity or a delay time in accordance with the position at which the region of interest ROI is set can improve the accuracy of superimposition and improve the image quality of the region of interest ROI.

The method of setting sound velocity is not particularly limited, and various well-known sound velocity setting methods commonly used in ultrasonic diagnostic apparatuses can be used. For example, a method for analyzing data in the region of interest ROI and calculating the sound velocity, a method for selecting a sound-velocity value in accordance with instructions input by an operator to the operation unit 32 or instructions to select a part such as muscle or fat from a menu, and other methods can be used.

In addition, when a region of interest ROI is set, the processing condition changing unit 23 may change a plurality of processing conditions among the number of superimpositions, the apodization factor, and the sound velocity (delay time).

In this case, the processing condition changing unit 23 may store a plurality of combinations for at least one of the conditions, namely, the number of superimpositions, the apodization factor, and the sound velocity (delay time), as presets in advance, and may call one of the stored presets in accordance with the set region of interest ROI.

Note that the configuration in which the processing conditions for multi-line processing within and outside the region of interest ROI are set different is not intended to be limiting. A configuration may be used in which different processing conditions for multi-line processing are set for a region within which the region of interest ROI is given an area having a predetermined width (blank area) and for the other region.

Alternatively, the processing condition changing unit 23 may change a processing condition for multi-line processing in accordance with the setting of a region of interest ROI, and change a condition for transmitting ultrasonic waves by using the transmitting unit 14 to obtain a transmit condition optimum to multi-line processing at the position of the region of interest ROI.

As a transmit condition to be changed, for example, the F value and/or the focal position can be changed to perform setting so that a transmit beam within the region of interest ROI can be spread to thereby increase the number of pieces of element data which can be effectively used for multi-line processing. In addition, the processing condition changing unit 23 can change the number of superimpositions for multi-line processing accordingly to provide further improvement in the accuracy of the multi-line processing.

Additionally, a setting information saving unit that saves a processing condition changed by the processing condition changing unit 23 may be included. Saving (storing) a changed processing condition makes it possible to easily reproduce the measurement under the same processing condition, which is preferable.

A signal processing method (a signal processing method of the present invention) in the ultrasonic diagnostic apparatus 10 will be described in detail hereinafter with reference to a flowchart illustrated in FIG. 9.

Note that a program of the present invention is a program for causing a computer included in the ultrasonic diagnostic apparatus 10 to execute the following signal processing method.

In the ultrasonic diagnostic apparatus 10, first, in accordance with instructions given from the control unit 30, in order to acquire element data, the transmitting unit 14 drives corresponding ultrasonic transducers (elements) of the probe 12 (the vibrator array 36) (with a predetermined number of apertures and at a predetermined aperture position) at a set transmit frequency to transmit an ultrasonic beam to the subject, an ultrasonic echo reflected by the subject is received by ultrasonic transducers (elements), and analog reception signals (analog element signals) are output to the receiving unit 16.

The receiving unit 16 performs predetermined processing such as amplification on the analog reception signals (analog element signals), and supplies the resulting signals to the A/D conversion unit 18.

The A/D conversion unit 18 performs A/D conversion on the analog reception signals (analog element signals) supplied from the receiving unit 16 to produce element data that is digital reception signals (digital element signals).

The element data is stored in the element data storage unit 20.

The element data processing unit 22 sequentially reads the element data stored in the element data storage unit 20 and performs multi-line processing to generate processed element data.

Specifically, as illustrated in parts (a) to (h) of FIG. 7 described above, the element data processing unit 22 calculates, for example, for an element of interest and elements adjacent to the element of interest, the delay times of the element data for the adjacent elements with respect to the element data for the element of interest, subjects the element data for the adjacent elements to delay-time correction and to a shift in the azimuth direction, and superimposes, on the element data for the element of interest, the element data for the adjacent elements on both sides thereof to generate processed element data for the element of interest.

The element data processing unit 22 superimposes element data for each of the pieces of element data corresponding to a predetermined plurality of lines to generate a plurality of pieces of processed element data. The element data processing unit 22 supplies the generated pieces of processed element data to the image generation unit 24. The image generation unit 24 generates an ultrasound image (B-mode image data) by using the pieces of processed element data. The generated ultrasound image is supplied to the display control unit 26 and is displayed on the display unit 28.

Here, if a region of interest ROI is set by the region-of-interest setting unit 21 in accordance with an input operation given from the operation unit 32, the processing condition changing unit 23 acquires information on the set region of interest ROI, such as the size and the position, and sets processing conditions in the element data processing unit 22 on the basis of the information on the region of interest ROI. The element data processing unit 22 performs processing of element data (multi-line processing) on frames, starting with the frame (transmission and reception) after new processing conditions have been set by the processing condition changing unit 23, on the basis of the processing conditions set in the processing condition changing unit 23 to generate a plurality of pieces of processed element data. The image generation unit 24 generates an ultrasound image (B-mode image data) by using the pieces of processed element data. The generated ultrasound image is supplied to the display control unit 26 and is displayed on the display unit 28.

In this manner, processing conditions for multi-line processing are set on the basis of information on the set region of interest ROI. This can prevent a reduction in frame rate while improving image quality in the region of interest ROI.

Note that, in the first embodiment described above, the processing condition changing unit 23 is configured to set, if a region of interest ROI is set, processing conditions in the element data processing unit 22 on the basis of the region of interest ROI; however, the present invention is not limited thereto. Alternatively, a configuration may be used in which, if a region of interest ROI is set, it is determined whether or not a processing condition is to be changed, and the processing condition changing unit 23 sets processing conditions if it is determined that a processing condition is to be changed.

FIG. 10 is a block diagram conceptually illustrating an example of the configuration of an ultrasonic diagnostic apparatus according to a second embodiment of the present invention.

Note that an ultrasonic diagnostic apparatus 100 illustrated in FIG. 10 has the same configuration as that of the ultrasonic diagnostic apparatus 10 illustrated in FIG. 1, except that the ultrasonic diagnostic apparatus 100 includes a processing condition change determination unit 102. Thus, the same components are assigned the same reference numerals and detailed descriptions thereof are omitted.

The processing condition change determination unit 102 is a part that determines whether or not to change a processing condition by using the processing condition changing unit 23 if a region of interest ROI is set by the region-of-interest setting unit 21.

Specifically, the processing condition change determination unit 102 determines that no processing condition is to be changed if it is determined that there is no need to change a processing condition for multi-line processing, such as when there is a small (or no) effect of multi-line processing, on the basis of information on the set region of interest ROI.

For example, if a region of interest ROI is set at a position that surrounds the focal position of the ultrasonic beam, an image at a position near the focal point has good image quality even if multi-line processing is not performed, which results in a small effect of multi-line processing. Thus, the processing condition change determination unit 102 determines that no processing condition in the element data processing unit 22 is to be changed.

Alternatively, if a region of interest is set over an entire screen, no improvement in image quality or improvement in frame rate is expected even if a processing condition is changed. Thus, the processing condition change determination unit 102 determines that no processing condition in the element data processing unit 22 is to be changed.

In this manner, determination of whether or not to change a processing condition for multi-line processing on the basis of information on the region of interest ROI allows multi-line processing to be performed under more appropriate processing conditions, and can provide more improvement in the quality of an ultrasound image to be created.

Alternatively, the processing condition change determination unit 102 may be configured to display an indication of whether or not to change a processing condition on the display unit 28 or the like to determine whether or not to change a processing condition on the basis of an input operation made by an operator to the operation unit 32.

This configuration will be described using the block diagram illustrated in FIG. 10 and a flowchart illustrated in FIG. 11.

If a region of interest ROI is set by the region-of-interest setting unit 21, the processing condition changing unit 23 selects one preset of an appropriate processing condition on the basis of information on the set region of interest ROI, and supplies the selected preset to the processing condition change determination unit 102. The processing condition change determination unit 102 supplies to the display control unit 26 a signal for causing the display unit 28 to display an indication that prompts the input of instructions on whether or not to change the processing condition (preset).

When an operator performs an input operation on the operation unit 32, the processing condition change determination unit 102 determines whether or not to change the processing condition on the basis of instructions input from the operation unit 32, and supplies a determination result to the processing condition changing unit 23.

If the processing condition change determination unit 102 determines that no processing condition is to be changed, the processing condition changing unit 23 does not change the processing condition. That is, the element data processing unit 22 performs multi-line processing under the processing condition obtained before the setting of the region of interest ROI, and generates processed element data.

On the other hand, if the processing condition change determination unit 102 determines that the processing condition is to be changed, the processing condition changing unit 23 changes the processing condition in the element data processing unit 22 on the basis of the determination result. When the processing condition is changed, the element data processing unit 22 performs multi-line processing on the element data of the subsequent frames (the transmission and reception of ultrasonic waves) under the newly set processing condition to generate a plurality of pieces of processed element data. The image generation unit 24 generates an ultrasound image by using the pieces of processed element data, and displays the generated ultrasound image on the display unit 28.

Note that, in the example illustrated in FIG. 11, the processing condition change determination unit 102 is configured to select one appropriate processing condition (preset) and to cause the display unit 28 to display an indication that prompts the input of instructions on whether or not to change the processing condition (preset). This configuration, however, is not intended to be limiting, and two or more processing conditions (presets) may be displayed to allow an operator to select a processing condition (preset). For example, a processing condition for increasing the number of superimpositions for the region of interest ROI to increase image quality may be marked with an indication of "image quality priority", and a processing condition for reducing the number of superimpositions for the region other than the region of interest ROI to increase the frame rate may be marked with an indication of "frame rate priority" to allow an operator to select which of the image quality and the frame rate is given priority.

Alternatively, the processing condition change determination unit 102 may be configured to determine whether or not to change a processing condition for multi-line processing on the basis of information on the set region of interest ROI, and further to display an indication of whether or not to change a processing condition on the display unit 28 or the like to determine whether or not to change a processing condition on the basis of an input operation made by an operator to the operation unit 32.

Specifically, a description will be given using a flowchart illustrated in FIG. 12.

First, if a region of interest ROI is set by the region-of-interest setting unit 21, the processing condition changing unit 23 determines whether or not to change a processing condition on the basis of information on the set region of interest ROI.

For example, if the region of interest ROI includes a focal position, it is determined that no processing condition is to be changed, and ultrasonic waves are transmitted and received under the processing condition obtained prior to the setting of the region of interest ROI to acquire element data. The element data is then subjected to multi-line processing to generate an ultrasound image, and the ultrasound image is displayed on the display unit 28.

On the other hand, if it is determined that a processing condition is to be changed, the processing condition change determination unit 102 supplies to the display control unit 26 a signal for causing the display unit 28 to display an indication that prompts the input of instructions on whether or not to change a processing condition (preset) or a signal for displaying an indication that prompts the input of instructions on which of two or more processing conditions (preset) to select.

When an operator performs an input operation on the operation unit 32 on the basis of the indication on the display unit 28, the processing condition change determination unit 102 determines whether or not to change a processing condition or which preset to select, on the basis of instructions input from the operation unit 32, and supplies a determination result to the processing condition changing unit 23.

The processing condition changing unit 23 changes a processing condition in the element data processing unit 22 on the basis of the determination result. When a processing condition is changed, the element data processing unit 22 performs multi-line processing on the element data of the subsequent frames (transmissions and receptions of ultrasonic waves) under the newly set processing condition to generate a plurality of pieces of processed element data. The image generation unit 24 generates an ultrasound image by using the pieces of processed element data, and displays the generated ultrasound image on the display unit 28.

While the first embodiment is configured such that the element data processing unit 22 performs multi-line processing by using element data, the present invention is not limited thereto and a configuration may be used in which first reception data obtained by performing phasing addition on first element data is subjected to multi-line processing.

FIG. 13 conceptually illustrates in block diagram form an example of an ultrasonic diagnostic apparatus 110 according to a third embodiment of the present invention.

Note that the ultrasonic diagnostic apparatus 110 illustrated in FIG. 13 has the same configuration as that of the ultrasonic diagnostic apparatus 10 illustrated in FIG. 1, except that the ultrasonic diagnostic apparatus 110 includes a data processing unit 114 in place of the element data processing unit 22, and an image generation unit 116 in place of the image generation unit 24. Thus, the same components are assigned the same reference numerals and detailed descriptions thereof are omitted.

The ultrasonic diagnostic apparatus 110 includes the ultrasonic probe 12, the transmitting unit 14 and the receiving unit 16, which are connected to the ultrasonic probe 12, the A/D conversion unit 18, the element data storage unit 20, the region-of-interest setting unit 21, the data processing unit 114, the processing condition changing unit 23, the image generation unit 116, the display control unit 26, the display unit 28, the control unit 30, the operation unit 32, and the storage unit 34.

In FIG. 14, the configuration of the data processing unit 114 is conceptually illustrated using a block diagram.

The data processing unit 114 includes a phasing addition unit 118, the delay time calculation unit 48, and a superimposition processing unit 120.

The phasing addition unit 118 performs phasing addition on element data read from the element data storage unit 20 to perform a receive-focusing process, and generates first reception data (unprocessed reception data).

Here, the phasing addition unit 118 performs the receive-focusing process described above on a single piece of element data a plurality of times while changing an element used as a reference, that is, a reference line, to generate two or more pieces of unprocessed reception data for each piece of element data.

The superimposition processing unit 120 acquires the unprocessed reception data generated by the phasing addition unit 118, on the basis of information related to data processing, such as the number of pieces of data to be superimposed and the superimposition processing method.

Further, the superimposition processing unit 120 superimposes two or more pieces of unprocessed reception data in terms of reception time, that is, in such a manner that their times are aligned, on the basis of the delay times corresponding to the respective pieces of unprocessed reception data, which are calculated by the delay time calculation unit 48, to generate processed (second) reception data.

Specifically, the superimposition processing unit 120 superimposes, among the pieces of unprocessed reception data supplied from the phasing addition unit 118, pieces of unprocessed reception data subjected to phasing addition processing by using the same element as a reference in accordance with the times at which the respective ultrasonic transducers receive the ultrasonic echoes, and generates processed reception data corresponding to a piece of unprocessed reception data.

The phasing addition unit 118 and the superimposition processing unit 120 will be described in more detail using parts (a) to (i) of FIG. 15 and parts (a) to (h) of FIG. 16.

First, the phasing addition processing performed in the phasing addition unit 118 will be described in detail with reference to parts (a) to (i) of FIG. 15.

Parts (a), (d), and (g) of FIG. 15 are conceptual diagrams for describing individual receive elements, parts (b), (e), and (h) of FIG. 15 are conceptual diagrams illustrating element data obtained by each transmission and reception of ultrasonic waves, and parts (c), (f), and (i) of FIG. 15 are conceptual diagrams illustrating unprocessed reception data obtained by subjecting individual pieces of element data to phasing addition processing.

Note that parts (a) to (i) of FIG. 15 illustrate a state in which a reflection point is located on a line corresponding to the n-th element.

First, an example of the generation of two or more pieces of unprocessed reception data from a single piece of element data will be described with reference to parts (a) to (c) of FIG. 15.

Part (a) of FIG. 15 is a diagram conceptually illustrating the vibrator array 36 in which a plurality of elements are arranged. In part (a) of FIG. 15, the positions of the elements are represented with the letter "n" and receive elements are represented by hatching. That is, part (a) of FIG. 15 illustrates that the (n−4)-th to (n+4)-th elements are receive elements, with the n-th element being the central element.

Part (b) of FIG. 15 is a diagram conceptually illustrating element data acquired by the receive elements illustrated in part (a) of FIG. 15. In addition, the positions in part (b) of FIG. 15 are displayed so as to correspond to the positions of the receive elements illustrated in part (a) of FIG. 15.

Note that, in the following description, element data obtained by using the n-th element as the central element is referred to as the n-th element data.

The phasing addition unit 118 reads the n-th element data from the element data storage unit 20, and performs phasing addition processing by using the line corresponding to the n-th element (hereinafter also referred to as the n-th line) as a reference line to generate the n(n)-th unprocessed reception data depicted in the center in part (c) of FIG. 15. The phasing addition unit 118 further performs phasing addition processing on the n-th element data by using the (n−2)-th line as a reference line to generate the n(n−2)-th unprocessed reception data depicted to the left in part (c) of FIG. 15. Likewise, the phasing addition unit 118 performs phasing addition processing on the n-th element data by respectively using the (n−1)-th, (n+1)-th, and (n+2)-th lines as reference lines to generate the n(n−1)-th unprocessed reception data, the n(n+1)-th unprocessed reception data, and the n(n+2)-th unprocessed reception data.

Here, reception data generated by subjecting, for example, the x-th element data to phasing addition by using the y-th line as a reference is expressed herein as the x(y)-th reception data.

Specifically, the phasing addition unit 118 of this embodiment performs, for a single piece of element data, phasing addition processing on each of five lines in total, including the lines corresponding to two elements located to the left and right of the central element and the line corresponding to the central element of the receive elements corresponding to the element data, to generate five pieces of unprocessed reception data, as illustrated in part (c) of FIG. 15.

Accordingly, as illustrated in parts (d) to (f) of FIG. 15, for the (n−1)-th element data, phasing addition processing is performed on each of the (n−3)-th to (n+1)-th lines centered on the (n−1)-th line to generate five pieces of unprocessed reception data illustrated in part (f) of FIG. 15. In addition, as illustrated in parts (g) to (i) of FIG. 15, for the (n+1)-th element data, phasing addition processing is performed on each of the (n−1)-th to (n+3)-th lines centered on the (n+1)-th line to generate five pieces of unprocessed reception data illustrated in part (i) of FIG. 15.

In this way, the phasing addition unit 118 performs phasing addition processing on necessary element data a plurality of times to generate a plurality of pieces of unprocessed reception data.

The phasing addition unit 118 supplies the pieces of unprocessed reception data to the superimposition processing unit 120.

Note that the number of pieces of unprocessed reception data generated from a single piece of element data in the phasing addition unit 118 is not particularly limited and may be determined, as appropriate, in accordance with the performance of the apparatus, the required processing speed (such as the frame rate), the image quality, and so on.

In addition, it is also preferable that the phasing addition unit 118 generate, in accordance with the width of the ultrasonic beam, a number of pieces of unprocessed reception data corresponding to the number of lines corresponding to the width.

Specifically, it is preferable that, when the number of superimpositions in the superimposition processing performed in the superimposition processing unit 120, described below, is to be caused to vary in accordance with the width of the ultrasonic transmit beam, phasing addition be performed, for each piece of element data, by using, as a reference, the central element of the receive elements corresponding to the piece of element data in accordance with the number of superimpositions and, in addition, phasing addition processing be performed a number of times corresponding to the number of superimpositions with an element used as a reference of the phasing addition being shifted.

For example, when the number of superimpositions is 11, phasing addition processing is performed by using as references the central element of the receive elements corresponding to the element data to be processed and five elements located to the left and right of the central element.

This enables the effect of superimposition to be sufficiently exerted and can reduce the amount of data to be stored.

Note that, when the number of superimpositions in the data processing unit 114 varies depending on the depth, the phasing addition unit 118 may generate a plurality of pieces of unprocessed reception data by changing the number of times phasing addition processing is performed on a single piece of element data depending on the depth or may generate a number of pieces of unprocessed reception data corresponding to the maximum width of the ultrasonic beam regardless of the depth.

Specifically, it is preferable that the phasing addition unit 118 generate a number of pieces of unprocessed reception data corresponding to three to ten lines for a single piece of element data.

Next, the superimposition processing performed in the superimposition processing unit 120 will be described in detail using parts (a) to (h) of FIG. 16.

Parts (a) and (e) of FIG. 16 are each a conceptual diagram illustrating unprocessed reception data to be subjected to superimposition, parts (b) and (f) of FIG. 16 are conceptual diagrams for describing their delay times, parts (c) and (g) of FIG. 16 are conceptual diagrams for describing the state of superimposed unprocessed reception data, and parts (d) and (h) of FIG. 16 are conceptual diagrams for describing the result of superimposition of the unprocessed reception data.

Note that the example illustrated in parts (a) to (h) of FIG. 16 is an example in which the number of superimpositions in the superimposition processing unit 120 is five.

In addition, the unprocessed reception data illustrated in parts (a) and (e) of FIG. 16 is a conceptual representation of unprocessed reception data for which the reflection point is located on the n-th line.

As illustrated in part (a) of FIG. 16, in order to generate processed reception data corresponding to the n(n)-th unprocessed reception data, the superimposition processing unit 120 acquires five pieces of unprocessed reception data (the n−2(n)-th unprocessed reception data, the n−1(n)-th unprocessed reception data, the n(n)-th unprocessed reception data, the n+1(n)-th unprocessed reception data, and the n+2(n)-th unprocessed reception data), which are pieces of unprocessed reception data generated as a result of subjecting different pieces of element data to phasing addition processing by using the n-th line as a reference.

The superimposition processing unit 120 performs delay-time correction on each of the five pieces of unprocessed reception data on the basis of the delay time calculated by the delay time calculation unit 48 (part (b) of FIG. 16), superimposes the resulting pieces of unprocessed reception data (part (c) of FIG. 16), and sums or averages the resulting pieces of unprocessed reception data to generate processed reception data corresponding to the n(n)-th unprocessed reception data (part (d) of FIG. 16). The resulting processed reception data is processed reception data corresponding to the n-th element (line).

Here, if a region of interest ROI is set, the superimposition processing unit 120 performs superimposition processing on the basis of the processing conditions (the number of superimpositions, the apodization factor, and the sound velocity (delay time)) set by the processing condition changing unit 23 to generate processed reception data.

This can achieve the processing conditions optimum to the set region of interest ROI, improve the image quality of the region of interest ROI, and prevent a reduction in frame rate.

Similarly, in order to generate processed reception data corresponding to the (n−1)-th line, the superimposition processing unit 120 acquires five pieces of unprocessed reception data (part (e) of FIG. 16), which are generated as a result of performing phasing addition processing by using the (n−1)-th line as a reference.

The superimposition processing unit 120 performs delay-time correction on each of the five pieces of unprocessed reception data on the basis of the delay time (part (f) of FIG. 16), superimposes the resulting pieces of unprocessed reception data (part (g) of FIG. 16), and sums or averages the resulting pieces of unprocessed reception data to generate the (n−1)-th processed reception data (part (h) of FIG. 16).

Here, as in parts (a) to (d) of FIG. 16, if pieces of unprocessed element data on which phasing addition processing has been performed by using as a reference a line (the n-th line) on which the reflection point is located are subjected to delay-time correction and are then superimposed, the phases of the signals from the reflection point are matched. Thus, as a result of the superimposition processing, a value (high-brightness value) with a signal (true signal) from the reflection point being enhanced is exhibited. (Part (d) of FIG. 16).

In contrast, as in parts (e) to (h) of FIG. 16, if pieces of unprocessed element data on which phasing addition processing has been performed by using as a reference a line (the n−1)-th line) on which the reflection point is not located are subjected to delay-time correction, the phases of signals (ghost signals) from the reflection point are not matched. Thus, as a result of superimposition, the signals cancel each other out, resulting in a signal having a small value (part (h) of FIG. 16).

Also for the other elements (lines), two or more pieces of unprocessed reception data on which phasing addition processing has been performed by using as a reference a line corresponding to an element of interest, where the element of interest is each of these elements, are read and are subjected to superimposition processing based on the delay times to enhance true signals whilst allowing ghost signals to cancel out, thereby enabling a reduction in the effect of the ghost signals.

Accordingly, processed reception data is subjected to detection processing and the like to generate an ultrasound image. This enables an ultrasound image to be generated from reception data which is free of influence of ghosting and for which it is equivalent to saying that every point on a sound ray is brought into focus. Thus, a high-brightness, high-quality ultrasound image with good sharpness can be generated.

In this manner, it is also possible to perform superimposition processing (multi-line processing) by using unprocessed reception data obtained as a result of subjecting element data to phasing addition processing. Note that the configuration in which phasing addition processing is followed by superimposition processing is preferable because the amount of data to be held (stored) can be reduced.

The data processing unit 114 supplies the generated processed reception data to the image generation unit 116.

The image generation unit 116 includes the detection processing unit 40, the DSC 42, the image processing unit 44, and the image memory 46.

In the image generation unit 116, the detection processing unit 40 performs attenuation correction and envelope detection processing on the reception data to generate B-mode image data. In addition, the DSC 42 raster-converts the B-mode image data into image data that supports a normal television signal scanning system, and the image processing unit 44 performs predetermined processing such as gradation processing.

The image processing unit 44 stores the generated B-mode image data in the image memory 46, and/or delivers it to the display control unit 26 to display a B-mode image of the subject on the display unit 28.

While an acoustic wave processing apparatus, a program of the present invention have been described in detail, it is needless to say that the present invention is not limited to the examples described above and various improvements or modifications may be made within the scope not departing from the gist of the present invention.

For example, the element data storage unit 20, which stores element data for one image, may not be included and transmission and reception of ultrasonic waves may be performed, for a single element of interest, a required number of times every time multi-line processing is performed.

REFERENCE SIGNS LIST 10, 100, 110 ultrasonic diagnostic apparatus
12 (ultrasonic wave) probe
14 transmitting unit
16 receiving unit
18 A/D conversion unit
20 element data storage unit
21 region-of-interest setting unit
22 element data processing unit 23 processing condition changing unit
24, 116 image generation unit
26 display control unit
28 display unit
30 control unit
32 operation unit
34 storage unit
36 vibrator array
38, 118 phasing addition unit
40 detection processing unit
42 DSC
44 image processing unit
46 image memory
48 delay time calculation unit
49, 120 superimposition processing unit
52 element
54 reflection point
56, 64 ultrasonic beam
58 focal point
60 receive path
61 transmit path
62 element data
66 true element data
68 ghost element data
114 data processing unit

What is claimed is:

1. An acoustic wave processing apparatus comprising:
a probe unit having a plurality of elements arranged therein, the probe unit being configured to transmit an acoustic wave beam, receive an acoustic wave echo reflected by an inspection object that has received the transmitted acoustic wave beam, and output an analog element signal corresponding to the received acoustic wave echo; and
a processor configured to:
cause the probe unit to transmit the acoustic wave beam a plurality of times by using two or more elements among the plurality of elements as transmit elements to form a predetermined transmit focal point,
receive an acoustic echo corresponding to each transmission of the acoustic beam with two or more elements among the plurality of elements as reception elements, receive analog element signals output from the reception elements, and perform predetermined processing on the analog element signals,
perform A/D conversion on the analog element signals to convert the analog element signals to first element data as a digital element signal,
select two or more pieces of the first element data from among a plurality of pieces of the first element data output or from among a plurality of pieces of first reception data generated by performing phasing addition processing on the first element data, and perform multi-line processing to generate processed element data by conducting superimposition on the selected two or more pieces of the first element data or pieces of the first reception data;
set a region of interest in an imaging area, and
in a case where the region of interest is set, change a processing condition of the superimposition in the multi-line processing on the basis of information on the set region of interest,
wherein the processor is further configured to cause the probe unit to transmit the acoustic wave beam the plurality of times by changing an element serving as a center,
wherein the change of the processing condition of the superimposition in the multi-line processing is to change the number of pieces of the first element data or pieces of the first reception data to be superimposed on the basis of information on the set region of interest, and
wherein the processor is further configured to set the number of superimpositions in the multi-line processing within the region of interest different from the number of superimpositions in the multi-line processing within a region other than the region of interest.

2. The acoustic wave processing apparatus according to claim 1, wherein the processor further configured to select two or more pieces of first element data from among the plurality of pieces of first element data, and superimpose the selected two or more pieces of first element data in accordance with reception times at which the elements receive the acoustic wave echo and positions of the elements to generate second element data.

3. The acoustic wave processing apparatus according to claim 1, wherein the processor further configured to perform phasing addition on each of the pieces of first element data by using at least two elements as references to generate at least two pieces of first reception data for each of the pieces of first element data, and
select two or more pieces of first reception data from among the plurality of pieces of first reception data, and superimpose the selected two or more pieces of first reception data in accordance with reception times at which the elements receive the acoustic wave echo and positions of the elements to generate second reception data.

4. The acoustic wave processing apparatus according to claim 3, wherein the processor further configured to superimpose two or more pieces of first reception data being generated from the pieces of first element data, which are different from each other, and being generated by subjecting the pieces of first element data which are different from each other to phasing addition processing by using the same element as a reference for each piece of first element data which are different from each other subjected to phasing addition.

5. The acoustic wave processing apparatus according to claim 1, wherein the processor further configured to change the processing condition by changing at least one of an apodization factor, a sound velocity, and a delay time.

6. The acoustic wave processing apparatus according to claim 2, wherein the processor further configured to change the processing condition by changing at least one of an apodization factor, a sound velocity, and a delay time.

7. The acoustic wave processing apparatus according to claim 3, wherein the processor further configured to change the processing condition by changing at least one of an apodization factor, a sound velocity, and a delay time.

8. The acoustic wave processing apparatus according to claim 4, wherein the processor further configured to change the processing condition by changing at least one of an apodization factor, a sound velocity, and a delay time.

9. The acoustic wave processing apparatus according to claim 1, wherein the processor further configured to change the processing condition on the basis of information on at least one of a size, position, and shape of the set region of interest.

10. The acoustic wave processing apparatus according to claim 2, wherein the processor further configured to change the processing condition on the basis of information on at least one of a size, position, and shape of the set region of interest.

11. The acoustic wave processing apparatus according to claim 3, wherein the processor further configured to change the processing condition on the basis of information on at least one of a size, position, and shape of the set region of interest.

12. The acoustic wave processing apparatus according to claim 4, wherein the processor further configured to change the processing condition on the basis of information on at least one of a size, position, and shape of the set region of interest.

13. The acoustic wave processing apparatus according to claim 5, wherein the processor further configured to change the processing condition on the basis of information on at least one of a size, position, and shape of the set region of interest.

14. The acoustic wave processing apparatus according to claim 1, wherein the processor further configured to determine whether or not to change the processing condition in a case where the region of interest is updated.

15. The acoustic wave processing apparatus according to claim 14, wherein the processor further configured to determine whether or not to change the processing condition on the basis of information on the set region of interest.

16. The acoustic wave processing apparatus according to claim 14, wherein the processor further configured to determine whether or not to change the processing condition in accordance with an instruction input from an operation unit.

17. The acoustic wave processing apparatus according to claim 1, wherein the processor further configured to save a changed processing condition.

18. The acoustic wave processing apparatus according to claim 1, wherein the processor further configured to cause the probe unit to transmit the acoustic wave beam the plurality of times by changing a transmit direction of the acoustic wave beam.

19. A signal processing method for the acoustic wave processing apparatus according to claim 1 for examining an inspection object by using a probe unit having a plurality of elements arranged therein, the probe unit being configured to transmit an acoustic wave beam, receive an acoustic wave echo reflected by the inspection object, which has received the transmitted acoustic wave beam, and output an analog element signal corresponding to the received acoustic wave echo, the signal processing method comprising:
a transmitting step of transmitting the acoustic wave beam a plurality of times by using two or more elements among the plurality of elements of the probe unit as transmit elements to form a predetermined transmit focal point;
a receiving step of receiving an acoustic echo corresponding to each transmission of the acoustic beam with two or more elements among the plurality of elements as reception elements, receiving analog element signals output from the reception elements, and performing predetermined processing on the analog element signals;
an A/D conversion step of performing A/D conversion on the analog element signals processed in the receiving step to convert the analog element signals to first element data as a digital element signal;
a data processing step of selecting two or more pieces of the first element data from among a plurality of pieces of the first element data output in the A/D conversion step or from among a plurality of pieces of first reception data generated by performing phasing addition processing on the first element data, and performing multi-line processing to generate processed element data by conducting superimposition on the selected two or more pieces of the first element data or pieces of the first reception data;
a region-of-interest setting step of setting a region of interest in an imaging area; and
a processing condition changing step of changing a processing condition in the data processing step, in a case where the region of interest is set in the region-of-interest setting step, on the basis of information on the set region of interest,
wherein the probe unit is caused to transmit the acoustic wave beam the plurality of times by changing an element serving as a center,
wherein the changing the processing condition is to change the number of pieces of the first element data or pieces of the first reception data to be superimposed on the basis of information on the set region of interest, and
wherein the number of superimpositions in the multi-line processing within the region of interest is set different from the number of superimpositions in the multi-line processing within the region other than the region of interest.

20. A non-transitory computer readable recording medium storing a signal processing program for the acoustic wave processing apparatus according to claim 1, the signal processing program being a program for causing a computer to execute a signal processing method for the acoustic wave processing apparatus for examining an inspection object by using a probe unit having a plurality of elements arranged therein, the probe unit being configured to transmit an acoustic wave beam, receive an acoustic wave echo reflected by the inspection object, which has received the transmitted acoustic wave beam, and output an analog element signal corresponding to the received acoustic wave echo, the signal processing program causing the computer to execute:
a transmitting step of transmitting the acoustic wave beam a plurality of times by using two or more elements among the plurality of elements of the probe unit as transmit elements to form a predetermined transmit focal point;
a receiving step of receiving an acoustic echo corresponding to each transmission of the acoustic beam with two or more elements among the plurality of elements as reception elements, receiving analog element signals output from the reception elements, and performing predetermined processing on the analog element signals;
an A/D conversion step of performing A/D conversion on the analog element signals processed in the receiving step to convert the analog element signals to first element data as a digital element signal;
a data processing step of selecting two or more pieces of the first element data from among a plurality of pieces of the first element data output in the A/D conversion step or from among a plurality of pieces of first reception data generated by performing phasing addition processing on the first element data, and performing multi-line processing to generate processed element data by conducting superimposition on the selected two or more pieces of the first element data or pieces of the first reception data;
a region-of-interest setting step of setting a region of interest in an imaging area; and a processing condition changing step of changing a processing condition in the data processing step, in a case where the region of interest is set in the region-of-interest setting step, on the basis of information on the set region of interest, wherein the probe unit is caused to transmit the acoustic wave beam the plurality of times by changing an element serving as a center, wherein the changing the processing condition is to change the number of pieces of the first element data or pieces of the first reception data to be superimposed on the basis of information on the set region of interest, and wherein the number of superimpositions in the multi-line processing within the region of interest is set different from the number of superimpositions in the multi-line processing within the region other than the region of interest.

\* \* \* \* \*